(12) United States Patent
Searle

(10) Patent No.: US 9,851,286 B2
(45) Date of Patent: Dec. 26, 2017

(54) VISCOSITY TESTING SYSTEM AND METHOD OF USING THE SAME

(71) Applicant: Vibrac, LLC, Amherst, NH (US)

(72) Inventor: Robert Searle, Amherst, NH (US)

(73) Assignee: Vibrac, LLC, Amherst, NH (US)

( * ) Notice: Subject to any disclaimer, the term of this patent is extended or adjusted under 35 U.S.C. 154(b) by 1013 days.

(21) Appl. No.: 13/797,159

(22) Filed: Mar. 12, 2013

(65) Prior Publication Data

US 2013/0245968 A1 Sep. 19, 2013

Related U.S. Application Data

(60) Provisional application No. 61/610,098, filed on Mar. 13, 2012.

(51) Int. Cl.
*G01N 11/00* (2006.01)
*G01N 11/10* (2006.01)
*G01N 11/14* (2006.01)

(52) U.S. Cl.
CPC ............ *G01N 11/10* (2013.01); *G01N 11/14* (2013.01)

(58) Field of Classification Search
CPC ............................... G01N 11/10; G01N 11/00
USPC ..................... 702/50, 147; 73/54.37, 57, 54
See application file for complete search history.

(56) References Cited

U.S. PATENT DOCUMENTS

| | | | | |
|---|---|---|---|---|
| 4,484,468 A * | 11/1984 | Gau | ....................... | G01N 11/14 702/50 |
| 4,602,501 A * | 7/1986 | Hirata | ................... | G01N 11/10 73/54.23 |
| 5,152,182 A | 10/1992 | Searle | | |
| 5,503,003 A | 4/1996 | Brookfield | | |
| 5,659,234 A * | 8/1997 | Cresens | ................... | H02P 8/36 318/569 |
| 5,677,481 A | 10/1997 | Brown et al. | | |
| 6,141,625 A | 10/2000 | Smith et al. | | |
| 6,776,028 B1 * | 8/2004 | Lukay | .................... | G01N 11/14 73/54.28 |
| 8,850,874 B1 * | 10/2014 | Bi | .......................... | G01N 11/14 73/54.28 |
| 2002/0007666 A1 * | 1/2002 | Robinson | ............... | G01N 11/14 73/54.28 |
| 2004/0149019 A1 * | 8/2004 | Johnson | ................ | G01N 11/14 73/54.28 |
| 2007/0000716 A1 | 1/2007 | Ponziani | | |
| 2007/0113679 A1 | 5/2007 | Searle | | |
| 2008/0092668 A1 * | 4/2008 | Searle | ....................... | G01L 3/12 73/862.23 |
| 2013/0172507 A1 * | 7/2013 | Ebisawa | ................ | G01N 11/14 526/329.7 |
| 2013/0226473 A1 * | 8/2013 | Murphy | ................. | G01N 11/14 702/50 |

(Continued)

*Primary Examiner* — Eman Alkafawi
(74) *Attorney, Agent, or Firm* — Pierce Atwood LLP; Kevin M. Farrell; David J. Wilson

(57) ABSTRACT

A highly efficient, highly accurate controllable digital viscosity testing system is provided. The system incorporates a variable speed motor, a digital encoder, a beam-deflection and/or magnetic torque resistance for unidirectional or bi-directional measurement of shear, and an API recommended practice 13B-11ISO 10414-1 bob and rotor sleeve measurement device for submerging in a test sample to measure shear forces exerted by the test sample.

13 Claims, 17 Drawing Sheets

(56) References Cited

U.S. PATENT DOCUMENTS

2014/0137638 A1* 5/2014 Liberzon ............... G01N 11/14
73/54.28

* cited by examiner

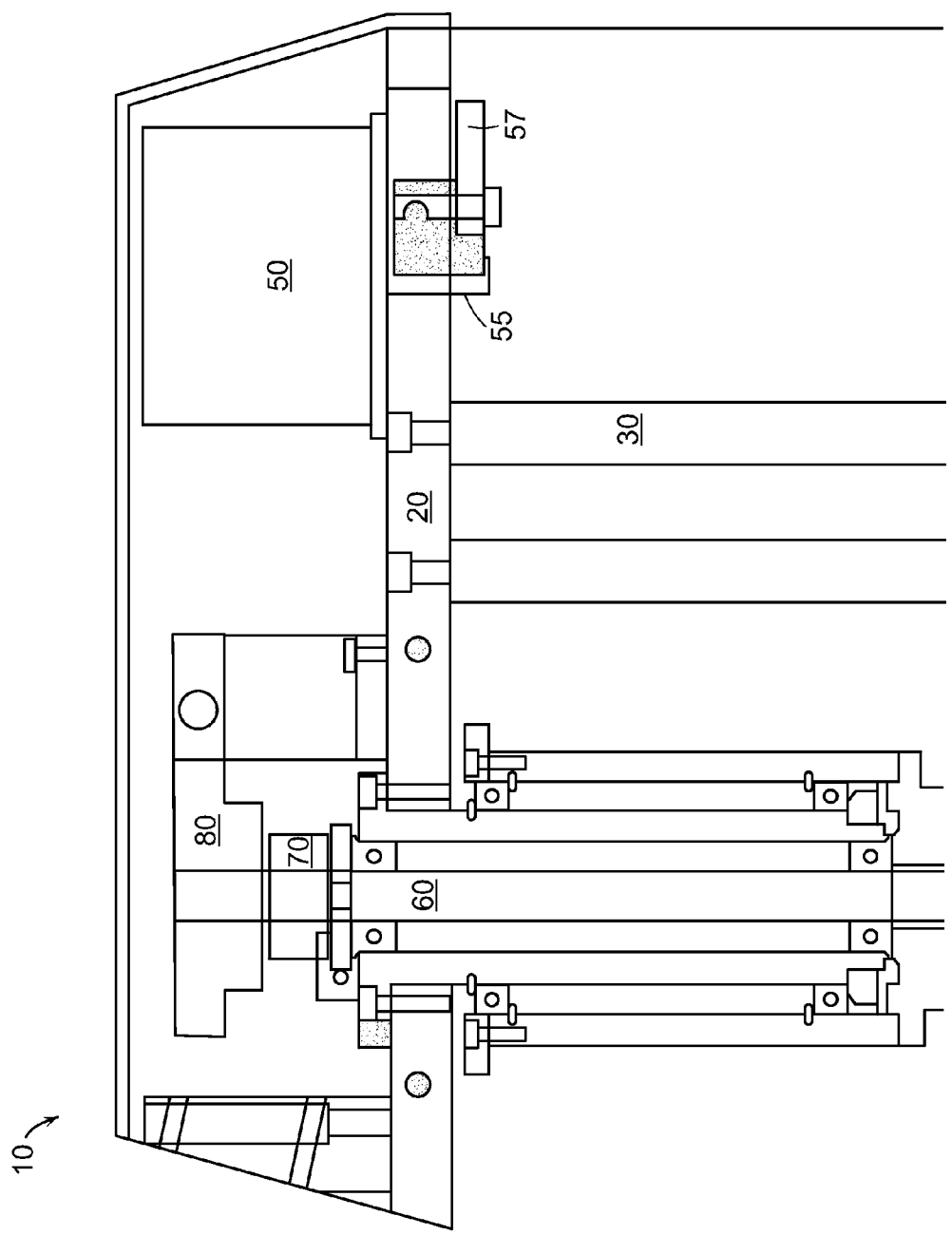

Sample Torque Measurement Specifications

Torque Range High: 30 oz-in
  Resolution: ±0.03 oz-in
Torque Range Low: 30 oz-in
  Resolution: ±0.001 oz-in Sample General Specifications Temp Range: 32° to 100°F (0° to 40°C)
Humidity Range: Up to 90% non-condensing
Height: 20 in (51 cm)
Width: 10 in (25 cm)
Depth: 15 in (38 cm)
Weight: 35 lbs (16 kg)
Input Power: 100-240 v AC 50/60 HZ

*Select A Test To Run*

*Touch Start*

*View Test Results*

FIG. 3B

Features

- Uses standard Rotors & Bobs
- Touch Screen Display
- Infinitely Variable Speed Control
- Multiple Test Programming

Main Menu

The Main Menu displays the primary features for the user.

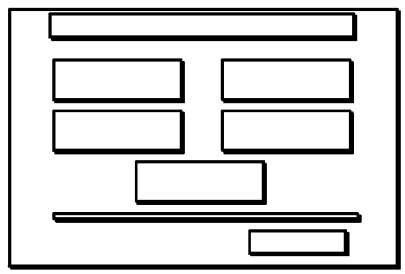

Selecting A Test

A user-friendly menu displays the library of tests that have been created to make the operator's job simple and efficient. There are no size limitations on the size of the library and a USB backup feature is included.

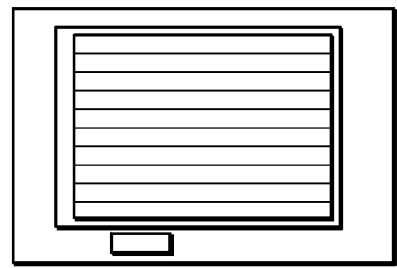

System Options

This menu enables the user to select the special features that best suit the viscosity test to be performed.

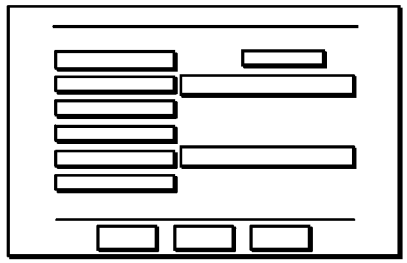

Test Sequence Screen

In the Test Sequence Screen the user can create a viscosity test with multiple steps in either the clockwise or counter-clockwise direction, or create tests that include steps in both directions, including oscillating test. Also, in this screen the operator will select the Rotor and Bob to be used as well as selecting the torque range for greatest accuracy.

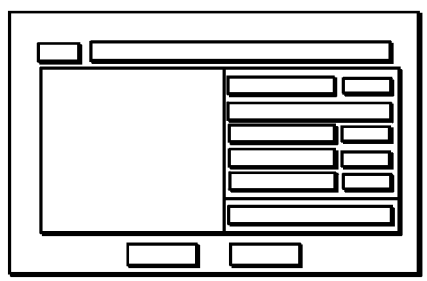

VISCOSITY TESTING SYSTEM AND METHOD OF USING THE SAME

CROSS REFERENCE TO RELATED APPLICATION

The present application is related to and claims benefit of priority to U.S. Provisional Patent Application No. 61/610,098 filed on Mar. 13, 2012. The content of that application is incorporated herein by reference.

BACKGROUND

1. Field of the Invention

The present disclosure relates generally to viscometers and more particularly to highly accurate and portable digital viscosity testing devices deployable in the field for unidirectional testing, bidirectional testing, and/or oscillation testing of fluid, slurry, and/or gel viscosity.

2. Discussion of Background Information

Viscosity testing is useful in a number of applications including, for example, the production of liquid compositions, cement slurries, gels, well drilling mud, viscous food and/or beverage products, pharmaceuticals, cosmetics, consumer products, paints, crude oil, etc. Testing samples of viscous substances, especially substances produced in batches, requires a high degree of accuracy both in measurement and analysis to insure proper formulation of the viscous substance. For example, cement slurries employed in securing oil well casings require frequent monitoring and testing in accordance with exact procedures and testing device standards that are designed to prevent catastrophic failure.

Viscosity testing devices exist for industry applications and industries have generated precise equipment specifications and testing requirements. For example, American Petroleum Institute Standard (API) API 13B-1/ISO 10414-1 provides precise measurement device dimensions and instructions for employing a measurement device to determine plastic viscosity and yield point of water-based drilling fluids. Petroleum drillers apply this standard, for example, to testing the oil well drilling mud used in the formation of oil wells. In accordance with API 13B-1/ISO 10414-1, a viscosity testing device may employ a bob of diameter 34.49 millimeters within a concentric rotor sleeve which may have an inside diameter of 36.83 millimeters. When submerged in a test sample, the rotor sleeve rotates and fluid shear forces applied to the bob impart torque on a shaft suspending the bob. In turn, in most devices, the shaft connects to a torsion spring for measuring resistance.

Standard viscosity testers, such as those provided by Fann® Instrument Company, provide visual pointer and increment type scales for reading a scale output measurement determined by the torque imparted on the torsion spring. These visual, incremented measurement scales bounce and/or jiggle in response to the vibration of moving parts during testing, thereby requiring a best guess as to a center point within a reading range. Further adding to inaccuracy and inefficiency, such scale readings require additional calculations to determine viscosity and do not provide a direct, simply viewed output reading of viscosity. Additionally, these standard analog viscosity testing devices incorporate analog transducers that drift with time and temperature, adding to the inaccuracy of test results. Additionally, these standard measurement systems lack sufficient precision for accurately testing highly viscous substances.

The API standards further require sampling viscosity at various speeds of rotation of the rotor sleeve. Most standard devices require that a user turn off the system motor and manually change gears on a standard two-speed motor, further delaying test efficiency. Some devices even employ a hand crank for varying rotor speed under inherently inconsistent human power, thereby introducing the variable of human error into the testing process. Furthermore, most viscometers are unidirectional and fail to accommodate accurate, repeatable bidirectional and/or oscillation testing of materials, like gels, that require such testing to determine viscosity and setting rate.

A need, therefore, exists for a system that preferably adheres to existing API standards and enables reliable, accurate and efficient testing of a wide range of viscous substances and gels. A need further exists for such a system that is easily controlled to produce a reliable and repeatable precise response by a computer controlled drive system that automatically changes speed and functions continuously and without interruption while running through a programmed routine. A need exists for such a device in a portable form for use in harsh, often hot and humid field environments such as those on oil rigs or manufacturing floors.

SUMMARY OF THE INVENTION

The present disclosure solves the problems associated with standard viscosity testing devices, particularly those deployed under harsh field testing conditions, such as those present on an oil rig or a manufacturing floor. Various embodiments of the present disclosure include an entirely digital, portable viscosity measurement system.

In one aspect, at least one embodiment described herein provides a digital viscosity measurement system. The digital viscosity measurement system includes a variable speed drive operatively coupled to a drive shaft. The digital viscosity measurement system also includes a drive coupling member for operatively coupling a rotating sleeve member to the drive shaft. The digital viscosity measurement system also includes a measurement device positioned concentric with the rotating sleeve member and coupled to a lower portion of a torque transmitting shaft, the torque transmitting shaft rotatably coupled with the measurement device. The digital viscosity measurement system also includes a digital encoder configured to measure a torque applied to the torque transmitting shaft by the measurement device.

Any of the aspects and/or embodiments described herein can include one or more of the following embodiments. In some embodiments, the digital viscosity measurement system also includes a processor mounted to the digital viscosity measurement system in communication with the variable speed drive for varying speed and in communication with the encoder for calculating viscosity based on a measured magnitude of torque applied to the torque transmitting shaft by one or more shear forces arising between the rotating sleeve member and the measurement device. In some embodiments, the digital viscosity measurement system also includes an electronic display member in communication with the processor for displaying a viscosity output and enabling selective control of the variable speed drive. In some embodiments, the measurement device is an API standard-compatible submersible bob member.

In some embodiments, the digital viscosity measurement system also includes a cantilevered support member mounted perpendicular to a vertical support column, the torque transmitting shaft being rotatably mounted through and extending downward from the cantilevered support member and the variable speed drive mounted atop the cantilevered support member, the drive shaft extending downward through the cantilevered support member and engaging with a rotatable drive member mounted therebeneath, wherein the rotatable drive member is operatively coupled with the drive coupling member. In some embodiments, the digital viscosity measurement system also includes a base member mounted perpendicularly to the vertical support column in parallel with the cantilevered support member. In some embodiments, the digital viscosity measurement system also includes a temperature probe positioned adjacent to the rotating sleeve member. In some embodiments, the digital viscosity measurement system also includes a force transmitting member affixed to the torque transmitting shaft. In some embodiments, the digital viscosity measurement system also includes at least one flexible beam positioned to be deflected by a rotation of the force transmitting member. In some embodiments, the at least one flexible beam includes first and second parallel flexible beams affixed at one end only atop the cantilevered support member. In some embodiments, the force transmitting member has a first end affixed to the torque transmitting shaft so as to rotate therewith and a second end extending between and adjacent to the parallel flexible beams so that rotation of the force transmitting member by the torque transmitting shaft will deflect one or the other of the parallel flexible beams depending upon the direction of rotation of the force transmitting member, each of the parallel flexible beams having the capability when deflected of applying a restoring force to the force-transmitting member and torque transmitting shaft. In some embodiments, the digital encoder produces an output signal that varies as a function of a degree of rotation of the torque transmitting shaft and of a known torque required to cause relative deflection of the at least one flexible member.

In some embodiments, the digital viscosity measurement system also includes a support surface oriented perpendicularly to the torque transmitting shaft. In some embodiments, the digital viscosity measurement system also includes opposite polarity magnets fixed to the support surface. In some embodiments, the digital viscosity measurement system also includes a rotatable magnet arm configured to be rotated by the torque transmitting shaft and disposed between the opposite polarity magnets, the rotatable magnet arm having a first end with a rotatable magnet disposed thereon between the opposite polarity magnets. In some embodiments, the digital viscosity measurement system also includes a rotatable magnetized member extending from a second end of the magnetic arm. In some embodiments, the digital viscosity measurement system also includes a fixed magnetized member disposed adjacent the rotatable magnetized member and having an opposite polarity than the rotatable magnetized member such that the rotatable magnetized member is attached to the fixed magnetized member for zeroing a rotation of the torque transmitting shaft. In some embodiments, the fixed magnetized member and the rotatable magnetized member are each selected from a group consisting of a magnetized shim and a magnetized needle. In some embodiments, the digital encoder produces an output signal that varies as a function of a degree of rotation of the torque transmitting shaft and of a known torque required to cause relative deflection of the rotatable magnet arm.

In some embodiments, the digital viscosity measurement system also includes a second rotatable magnet disposed on a second end of the rotatable magnet arm between the opposite polarity magnets. In some embodiments, the digital viscosity measurement system also includes a magnetic spring arm having a first end affixed to at least one of the rotatable magnet arm or the torque transmitting shaft so as to rotate therewith and extending parallel to the rotatable magnet arm. In some embodiments, the digital viscosity measurement system also includes a magnetic positioning element affixed to a second end portion of the magnetic spring arm. In some embodiments, the digital viscosity measurement system also includes an electromagnet mounted to the support surface. In some embodiments, the digital viscosity measurement system also includes a receiving slot defined on an upper surface of the electromagnet, wherein magnetizing the electromagnet draws the magnetic positioning element into engagement with the receiving slot for zeroing a rotation of the torque transmitting shaft. In some embodiments, the digital viscosity measurement system also includes a physical stop positioned to limit a rotational travel of the rotatable magnet arm in one direction.

In one aspect, at least one embodiment described herein provides a method for testing a viscosity of a fluidic or gelatinous substance. The method includes providing a viscosity measurement system. The viscosity measurement system includes a variable speed drive operatively coupled to a drive shaft. The viscosity measurement system also includes a drive coupling member for operatively coupling a rotating sleeve member to the drive shaft. The viscosity measurement system also includes a measurement device positioned concentric with the rotating sleeve member and coupled to a lower portion of a torque transmitting shaft, the torque transmitting shaft rotatably coupled with the measurement device. The viscosity measurement system also includes a digital encoder configured to measure a torque applied to the torque transmitting shaft by the measurement device. The method also includes submerging the measurement device and the rotating sleeve member in a fluidic or gelatinous substance. The method also includes rotating the rotating sleeve member to generate at least one shear force on the measurement device. The method also includes measuring, using the digital encoder, a torque applied to the torque transmitting shaft by the measurement device. The method also includes calculating, on a processor, a viscosity of the fluidic or gelatinous substance based on the rotational speed of the rotating sleeve member and the torque measured by the encoder.

Any of the aspects and/or embodiments described herein can include one or more of the following embodiments. In some embodiments, the method also includes displaying a value of the viscosity on a digital display member. In some embodiments, the method also includes transmitting a value of the viscosity to a remote receiver.

BRIEF DESCRIPTION OF THE DRAWINGS

One will better understand these and other features, aspects, and advantages of the disclosure following a review of the description, appended claims, and accompanying drawings in which:

FIGS. 2A-2C are schematics illustrating side and top views of a digital viscosity measurement system in accordance with various embodiments.

FIGS. 3A and 3B are simulated screen imagery illustrating output displays of an electronic display member in accordance with various embodiments.

DETAILED DESCRIPTION

A digital viscosity testing/measurement system in accordance with various embodiments solves problems associated with state of the art analog viscometers having visual indicator scale outputs. A viscosity measurement system in accordance with various embodiments solves the efficiency and accuracy problems associated with standard viscosity testing devices, particularly those deployed under harsh field testing conditions, such as those present on an oil rig or manufacturing floor. Portions of the system mimic torque testing devices disclosed in U.S. Pat. Nos. 5,152,182 and 7,481,122, the entirety of which references are herein incorporated by reference.

Figure 1:
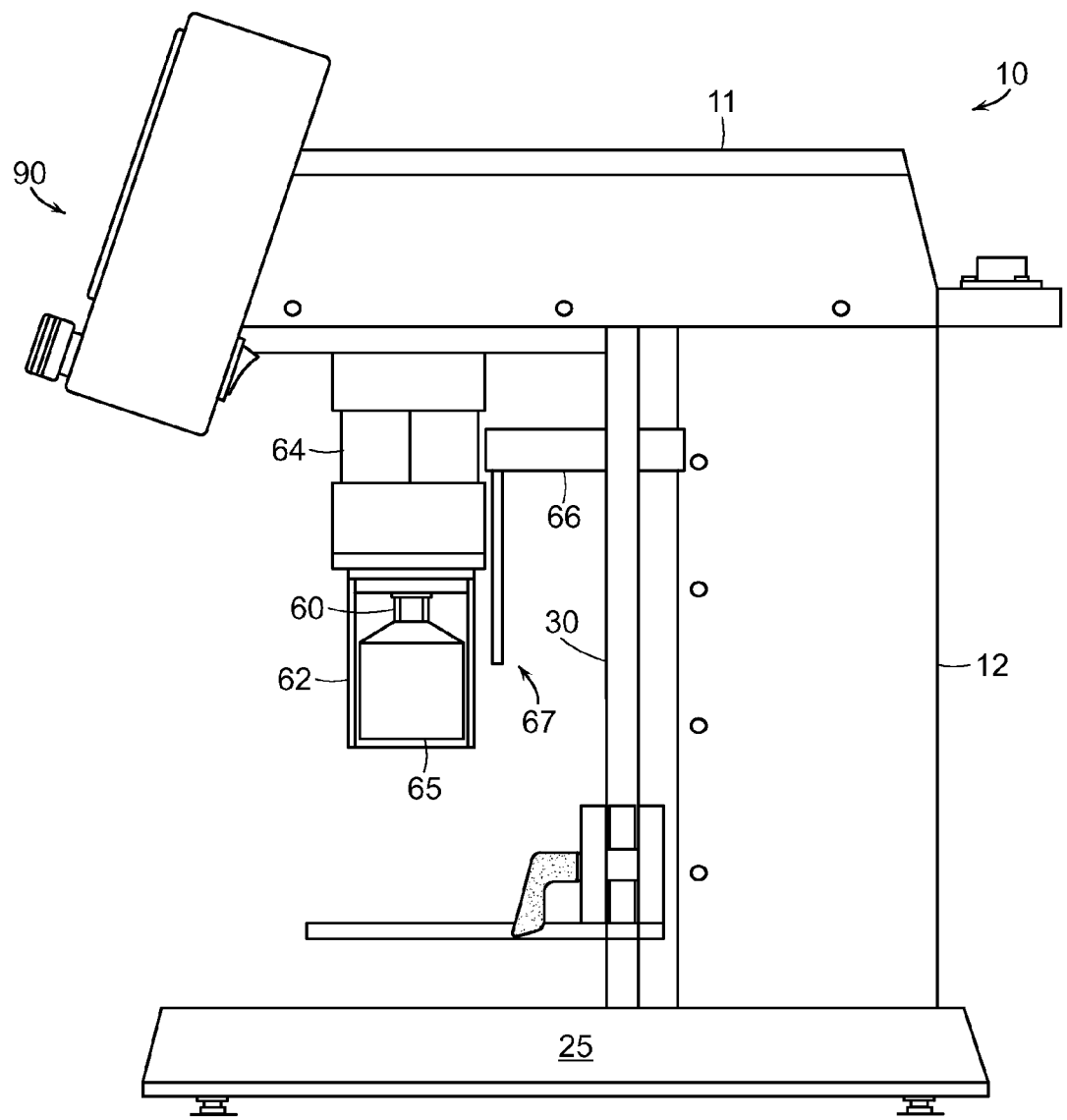
FIG. 1 is a schematic illustrating a side view of a digital viscosity measurement system in accordance with various embodiments.

As depicted in FIG. 1, a viscosity measurement system 10 in accordance with various embodiments may include a cantilevered support member 20 mounted to a vertical support column 30. The viscosity measurement system 10 and any components thereof may be of any size and/or weight but in various embodiments the viscosity measurement system 10 may be advantageously sized to be easily transportable. For example, the viscosity measurement system 10, in some embodiments, may occupy roughly one cubic foot and easily fit within a foam padded, wheeled transportation case, such a hard-shelled Pelican® case with durable wheels and a retractable pull handle. Additionally, as appropriate for various individual applications, the viscosity measurement system 10 may be configured to extract power from a standard power outlet (e.g., a 120V/60 Hz outlet), a battery source (advantageously allowing the viscosity measurement system 10 to function as a self-contained unit), and/or any other suitable electrical power supply.

In various embodiments, a torque transmitting shaft 60 rotatably mounts through, and extends downward from, the cantilevered support member 20. The cantilevered support member 20 effectively suspends the torque transmitting shaft 60 over a weighted base 25 to which the vertical support column 30 mounts. The weighted base 25 may, in various embodiments, provide stability to prevent vibration in the viscosity measurement system 10 during testing and thereby insures more accurate output. In various embodiments, the viscosity measurement system 10 weighs between ten (10) and sixty (60) pounds, preferably between twenty (20) and forty (40) pounds. In some embodiments the system weighs thirty-five (35) pounds, with the greatest portion of weight being distributed throughout the base 25 for added stability.

Upper casing 11 and lower casing 12, in various embodiments, mount to the cantilevered support member 20 and vertical support column 30 respectively. Such casings may keep dirt, dust, fluids, and other unwanted foreign matter from damaging internal components of the viscosity measurement system 10. In some embodiments, magnetic shielding may advantageously be provided in or on at least one of the upper casing 11 and/or the lower casing 12 to prevent external devices and objects (e.g., cell phones, transmitters, magnets, welding equipment) from interfering with the operation of the viscosity measurement system.

In various embodiments, a digital display member 90 is mounted to a free end of the cantilevered support member 20. Because the readout produced by the digital display member consists of digital indicia, the difficulties associated with reading measurement lines on a manually-read torsion spring activated scale are avoided. Accordingly, user error in reading a calculated viscosity measurement due to vibration can be eliminated by a viscosity measurement system 10 in accordance with various embodiments.

Turning now to the particular elements of the embodiment of a viscosity measurement system 10 shown in FIGS. 2A-2D, mounted atop the cantilevered support member 20 is at least one flexible beam 40 of known length and bending resistance. The at least one flexible beam 40 is affixed only at one end 42 so that the non-constrained end is free to move under the application of force. The at least one flexible beam 40 therefore flexes and bends under load applied to the free end. The embodiment of FIGS. 2A-2D includes two parallel flexible beams 40a, 40b, spaced apart, which are affixed only at one end 42. The combined first and second parallel flexible beams 40a, 40b respond to forces applied in two directions.

In addition to the parallel flexible beams 40a, 40b, other elements mount to the top surface of the cantilevered support member 20. In various embodiments, a force transmitting member 70 mounts atop the cantilevered support member 20 and has a first end 72 affixed to the torque transmitting shaft 60 so as to rotate therewith and a second end 74 extending between and adjacent to the parallel flexible beams 40a, 40b. In various embodiments, the first and second parallel flexible beams 40a, 40b are spaced apart at a distance just great enough to accommodate the width of the force transmitting member 70 in a resting position. Rotation of the force transmitting member 70 by the torque transmitting shaft 60 immediately deflects one or the other of the parallel flexible beams 40a, 40b, depending upon the direction of rotation of the force transmitting member 70. Each of the parallel flexible beams 40a, 40b has the capability when deflected of applying a restoring force to the force transmitting member 70 and torque transmitting shaft 60.

Also mounted atop the cantilevered support member 20 is a variable speed drive 50 that is adapted for computer automated multistep sequencing through a range of rotational drive speeds (RPMs). The variable speed drive 50 has engaged therewith a drive shaft 55 extending downward through the cantilevered support member 20. The drive shaft 55 engages with a rotatable drive member 57 mounted beneath the cantilevered support member 20. The drive shaft 55 lies along an axis distinct from the axis of the torque transmitting shaft 60, and in various embodiments, the two axes are parallel to one another.

In various embodiments, the system further comprises a digital encoder 80 (e.g., a digital encoder and/or a digital optical encoder) mounted atop the cantilevered support member 20 and coupled to the torque transmitting shaft 60 for producing an output signal that varies as a function of the degree of rotation of the torque transmitting shaft 60 and deflection resistance force of the first and second parallel flexible beams 40a, 40b. In various embodiments the digital encoder 80 may, for example, be a digital incremental magnetic encoder having a resolution of 2048 pulses per degree after interpolation. An encoder sensor head 81 is located proximate to the digital encoder 80 for taking readings. Mounting the encoder 80 to the torque transmitting shaft further adds space economy to the compact digital viscosity measurement system 10, which aids in portability and eliminates any additional moving parts, such as an encoder shaft and connection belt. Such additional elements would claim additional space, add weight, and present additional integrated moving parts that could seize or otherwise fail catastrophically in use under harsh testing environment conditions.

In operation, the digital viscosity measurement system 10 comprises elements that contact a test sample. A mechanical measurement device 65 applies torque to the shaft when submerged in a fluid or viscous composition. In various embodiments, the measurement device 65 comprises an API standard-compatible submersible bob member coupled to the lower end of the torque transmitting shaft 60 and a submersible rotating sleeve member 62 mounted about the torque-transmitting shaft 60 and measurement device 65 and coupled to the rotatable drive member 57. The rotating sleeve member 62 may be indirectly or directly coupled via a drive coupling member 58 to the rotatable drive member 57. The drive coupling member 58 may be, for example, a belt or chain therewith engaged. When the variable speed drive 50 and drive shaft 55 rotate, the rotatable drive member 57 thereon can then rotate the rotatable sleeve 62 via the drive coupling member 58 transmitting the rotational force. In some embodiments, the rotatable sleeve 62 may be directly coupled to a rotor shaft 64 (e.g., a barrel shaft concentric with and external to the torque transmitting shaft 60 as shown in FIG. 1), which is coupled to a rotatable drive member 57 via a drive coupling member 58. In such embodiments, the rotatable drive member 57 may rotate the rotor shaft 64 via drive coupling member 58, thereby rotating the rotatable sleeve 62.

Turning now to the particulars of the variable speed drive 50, the digital viscosity measurement system 10 provides substantial improvements over prior art viscosity testing devices. The integration of a computer controlled variable speed drive 50 mounted on a unique axis enables a user to program the digital viscosity measurement system 10 and run automatically through a series of speeds and time intervals to execute a series of required, industry standard and/or uniquely programmed tests. The programmability and computer control of the variable speed drive 50 enables accurate, efficiently measured test results. Additionally, the entirely digital composition of the viscosity measurement system 10 enables computer automation of multistep sequencing and bi-directional, oscillation testing, which is useful, for example, for testing a gel setting rate.

This precise, repeatable, and accurate controllability of the variable speed drive 50 stems in part from the variable speed drive 50 requiring no gearing changes and avoiding load issues associated with geared motors. In various embodiments, the variable speed drive may be, for example, a 24V DC stepping motor coupled with a compact, lightweight, low-vibration microstepping driver. The electronically controlled drive in the variable speed drive motor 50 produces a consistent output with smooth transitions between drive shaft 55 rotational speeds. The highly controllable variable speed drive 50 in accordance with various embodiments is functional through a large range of speeds while precisely achieving those desired speeds. For example, various embodiments, detailed in FIGS. 3A-3B, produce accurate results over a large range of torque measurements. In various embodiments depicted by FIGS. 3A-3B, the torque measurements range from 0 oz-in to 30 oz-in with resolutions respectfully ranging from a deviation one-one thousandth oz-in (±0.001) to three hundredth oz-in (±0.03).

Furthermore, integration of a computer controlled variable speed drive 10 enables the viscosity measurement system 10 to produce more accurate results while achieving a substantial time improvement over standard test devices. A standard viscosity test sequence executed in accordance with API 13B-1/ISO 10414-1 runs on the digital viscosity measurement system 10 for a duration of about 1 minute whereas state of the art test devices comparably produce test results in about 1 hour because of the high degree of human involvement required to change gears, read visual indicator scales and perform additional calculations. The digital viscosity measurement system 10 of the present disclosure therefore achieves a substantial improvement over prior art devices.

Figure 2B:
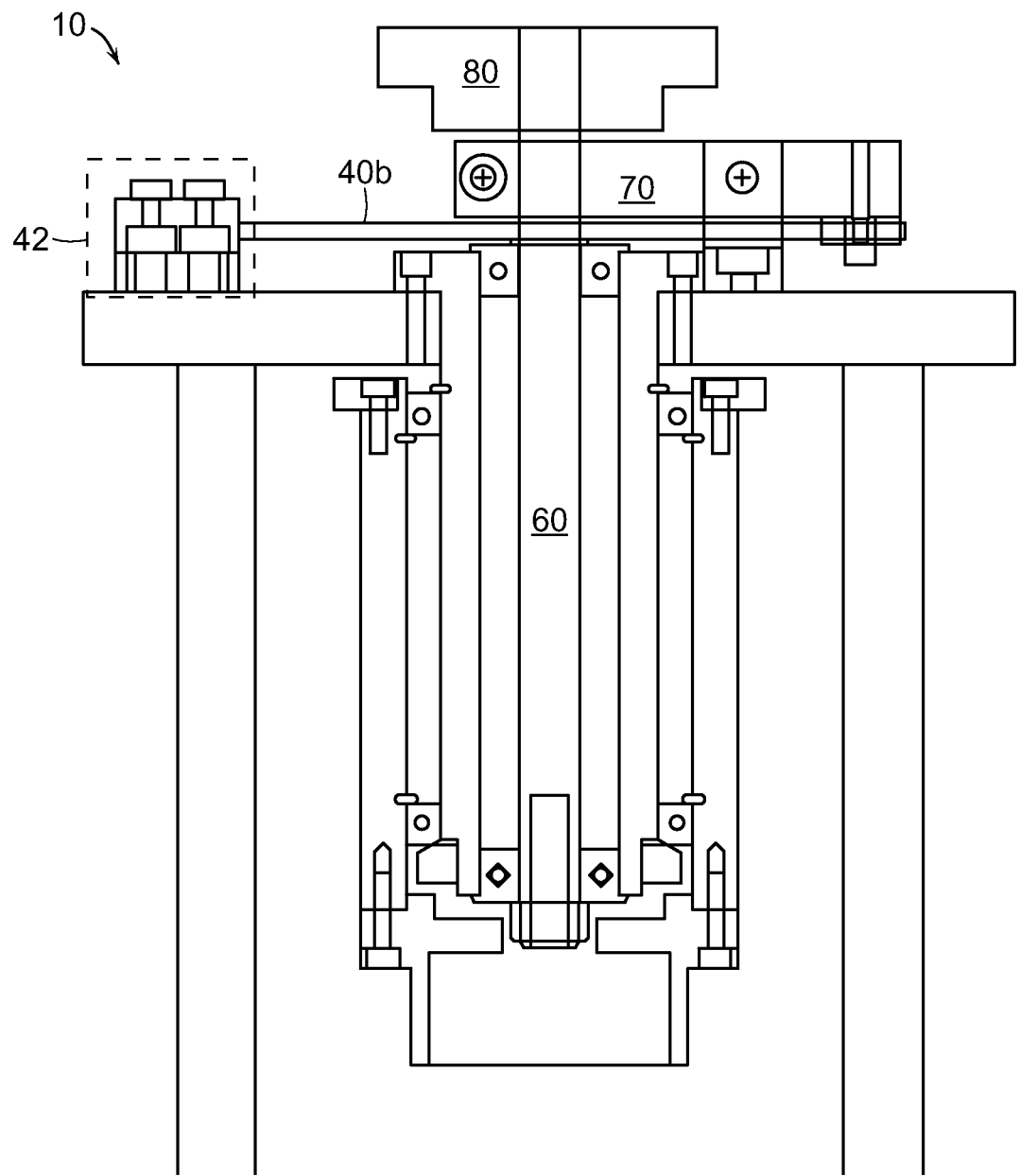
Figure 2C:
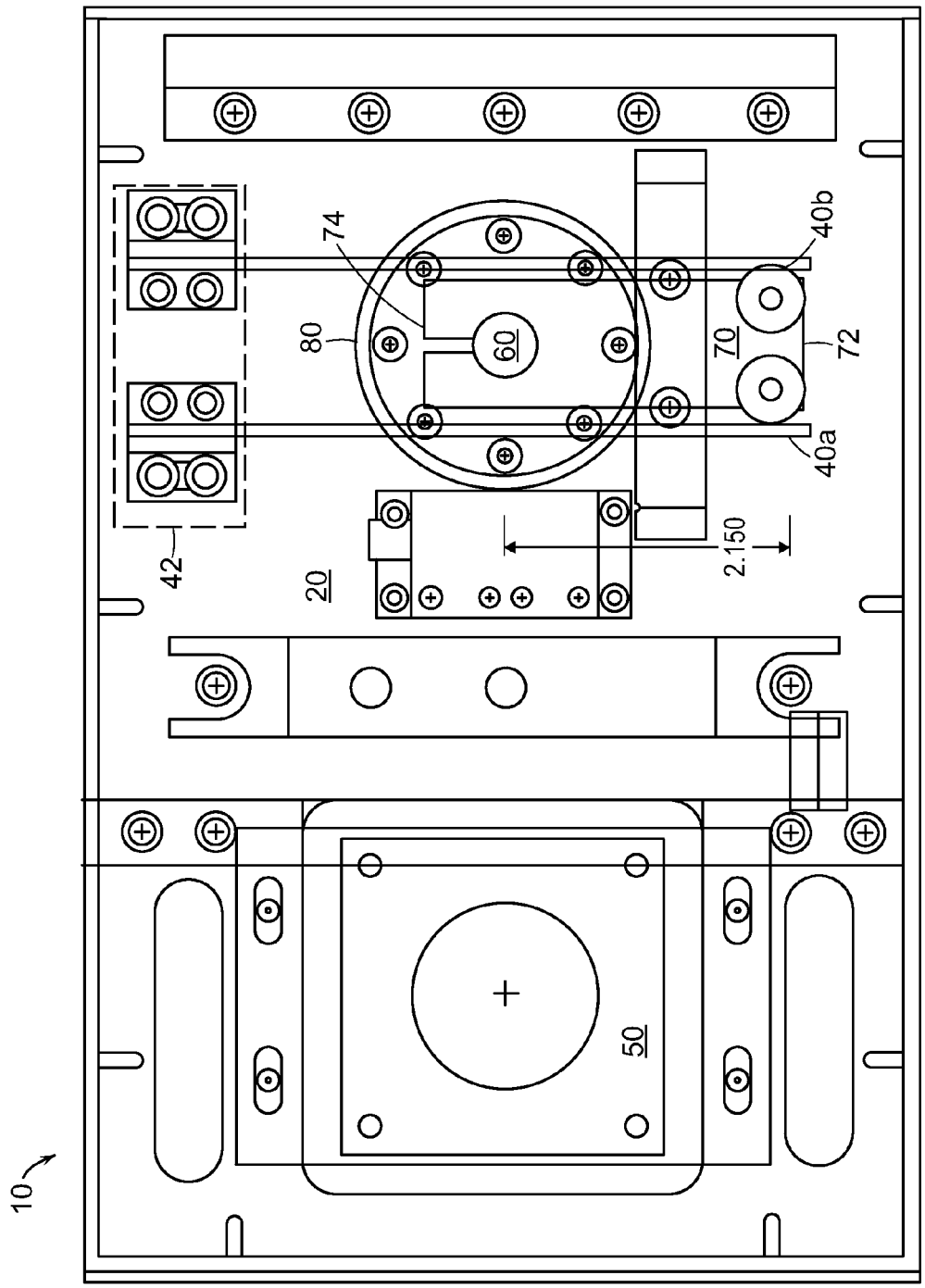
Figure 2D:
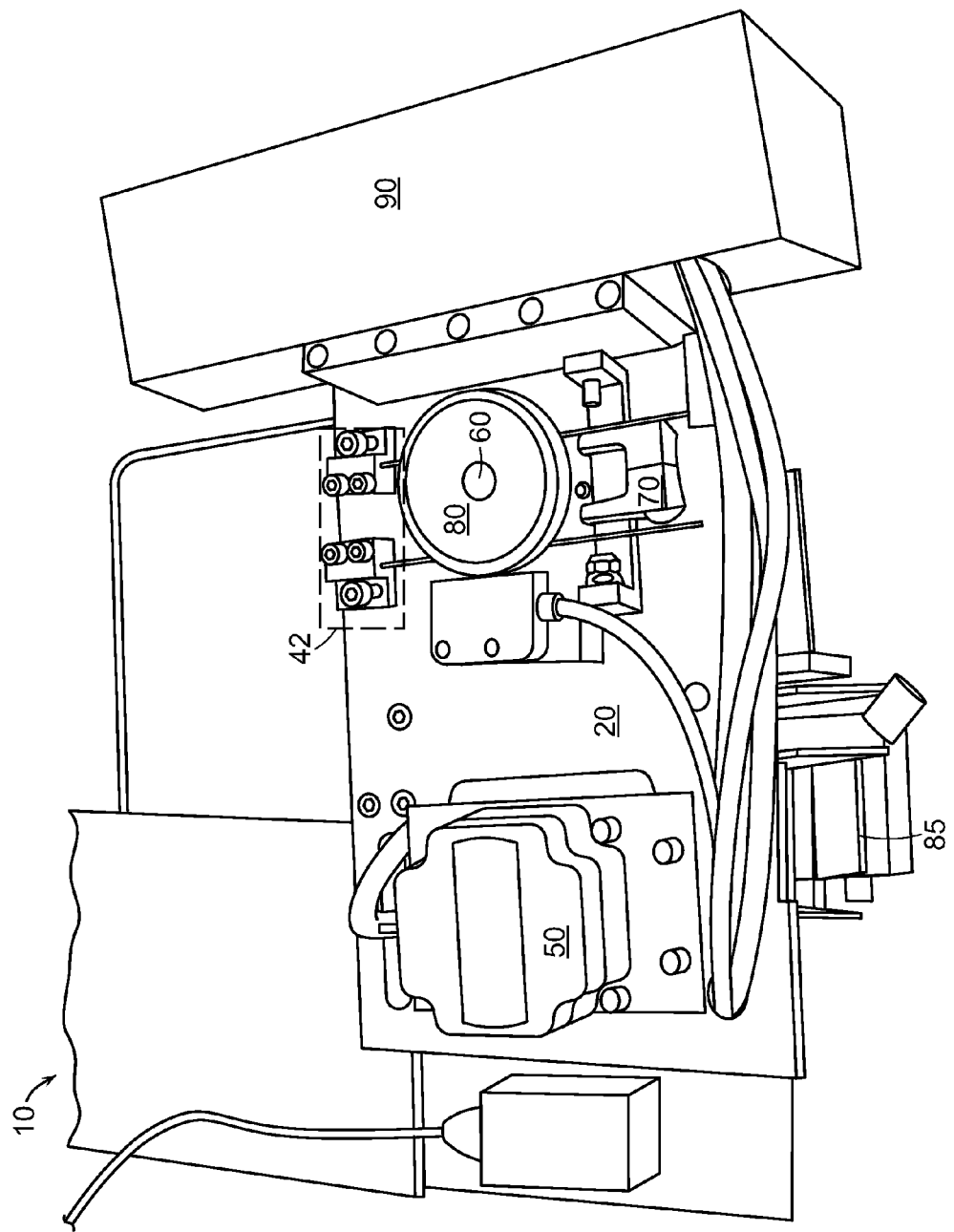
FIG. 2D is an isometric view illustrating a top view of a viscosity measurement system in accordance with various embodiments

In various compact portable embodiments, a processor 85, best shown in FIG. 2D, mounts directly to the measurement system and communicates with the encoder 80 via wired means. The processor 85 controls the variable speed drive 70, receives the output measurements from the encoder 80 and calculates viscosity based on measured magnitude of torque applied to the torque-transmitting shaft 60 by the shear forces arising in the fluid or viscous composition disposed between the rotating sleeve member and bob member. Alternate embodiments of the viscosity measurement system 10 may include wireless communication means and transmitter/receiver devices for remote communication of measurement data to the processor for further computation and analysis.

Figure 3A:
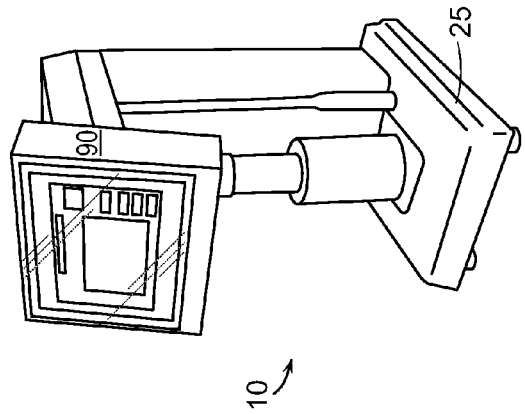
Figure 3A:
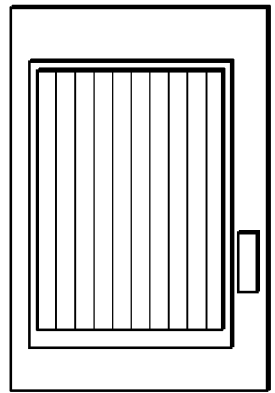
Figure 3A:
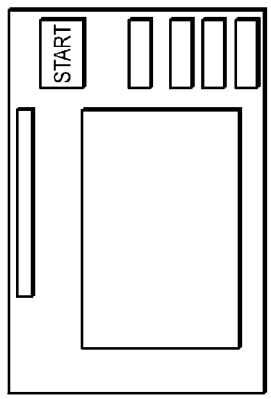
Figure 3A:
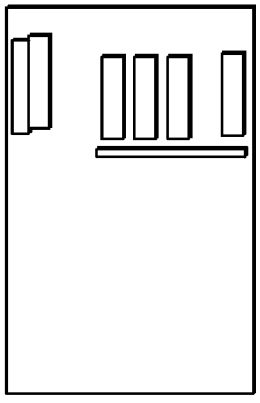
Figure 4:
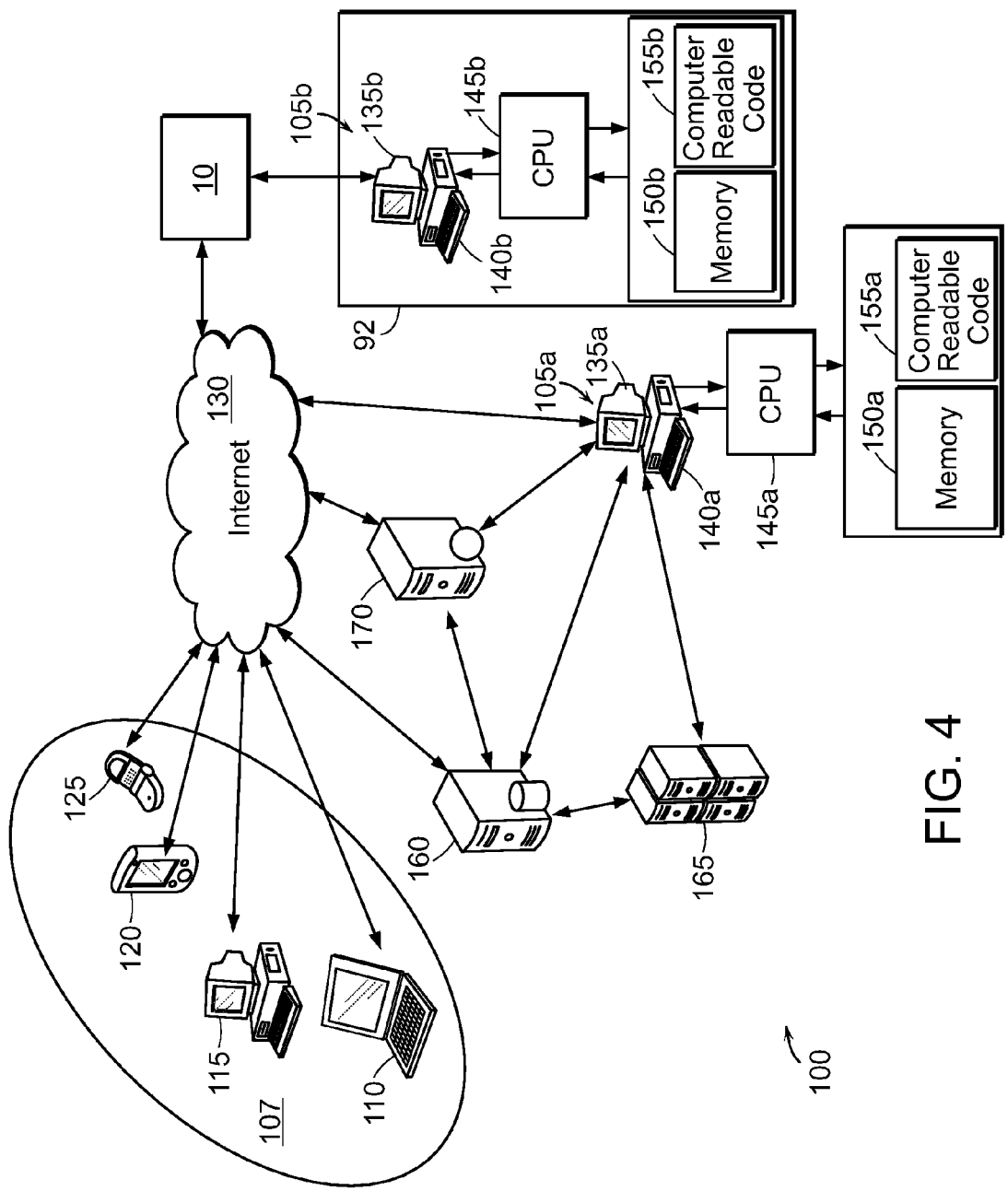
FIG. 4 is a relationship diagram illustrating a computer implemented viscosity measurement system in accordance with various embodiments.

In various portable embodiments, the system provides an electronic display member 90 that is coupled to the cantilevered support member 20 for communicating with the processor 80, displaying viscosity output and enabling selective control of the variable speed drive 50. In other embodiments, the display member 90 may be in wireless communication with the processor 85 and accordingly disposed remotely from the remainder of the measurement system 10 as indicated in FIG. 4 by the broken line leading to standard computing elements 92. FIGS. 3A-3B depict sample screen shots from the display member 90 which enables selection of tests and test parameters in addition to displaying output measurement results.

In various embodiments, the display member 90 comprises a touch screen, thereby eliminating the need to connect the viscosity measurement system 10 to an external processor for test program selection. This adds to the self-contained, fully functional, portable design of the viscosity measurement system 10. In various embodiments, because the viscosity measurement system 10 can be entirely digital and programmable, the system 10 in accordance with various embodiments may provide for remotely driven testing and remote monitoring of test results. Such remotely driven testing and remote monitoring can be achieved via communication between the system 10 and, for example, a remote computing device (e.g., any of 110, 115, 120, and 125 as shown in FIG. 4) through a computer network.

FIG. 4 depicts an overview of a computer implemented system 100 in accordance with various embodiments. The depicted system 100 includes an organization terminal 105 in communication with a plurality of user terminals 107 that are communicating through a computer network. Because the viscosity measurement system 10 is available on a global level, and because the Internet 130 is a global electronic communications network linking private and public networks and computers, the Internet 130 is an appropriate medium for facilitating uses and applications of the viscosity measurement system 10 in accordance with various embodiments. The plurality of user terminals 107 are preferably devices capable of communicating with the Internet 130 through wired or wireless means, devices for example such as a laptop computer 110, a stationary computer 115, a personal computing device (PCD) 120, and a cellular telephone 125.

The organization terminal 105 is preferably a computer that comprises elements typical of a computing system. These elements include items such as a monitor 135, a keyboard 140, a processor such as a central processing unit (CPU) 145, and a memory storage area 150. The memory storage area 150 may be random access memory (RAM), or a combination of RAM and some removable memory storage means such as floppy disk, EPROMs, PROMs, or USB storage devices. The memory storage area 150 contains computer readable code, or software 155, for executing various functionalities of the viscosity measurement system 10. In various embodiments, the memory storage area 150 may be a database server 160 for an added level of security and more expansive storage capacity for storing aggregated data and test results. In an alternative embodiment, the organization terminal 105 optionally also may communicate with an application server 165 that stores and executes the software 155 and with a web server 170 that hosts an interactive website that dynamically displays relevant information for interacting with the viscosity measurement system 10.

Bi-directional routers (not shown) also may be disposed between each of the plurality of user terminals 107 and the Internet 130, and between the Internet 130 and the organization terminal 105. Additionally the laptop computer 110, stationary computer 115, peD 120, and cellular telephone 125 are shown by way of example only and an unlimited number of user terminals 107 may communicate with the organization terminal 105.

A user stationed at any of the user terminals and/or organization terminal 105 may communicate through the Internet 130 with the viscosity measurement system 10 to request test data and/or transmit test scripts for running a routine on the system 10. This increases visibility and awareness of on-site testing so that remotely located scientists and business people, for example, may monitor, aggregate and analyze data in real time. In the example of deployment of multiple viscosity measurement systems 10 across a plurality of oil well sites, remote monitoring allows a user at the organization terminal 105 to analyze and compare test data across a geographic region and easily identify any outlier data in real time. Someone analyzing a plurality of data across a plurality of oil rigs deployed throughout a geographic region therefore can determine whether outlier data is attributed to, for example, extreme humidity at one or more locations, or whether a composition test sample is completely incorrectly formulated at one or more sites.

One particularly useful application of the viscosity measurement system 10 in accordance with various embodiments is testing samples of cement slurry used in securing oil well casings. An improper cement slurry formulation could lead to catastrophic oil well failure if a casing were to dislodge. Testing cement slurry samples as batches of cement are mixed for deployment is a highly important step in the creation of secure oil wells, and integrating a highly precise, accurate, efficient viscometer such as viscosity measurement systems 10 in accordance with various embodiments is of great importance.

Turning now to FIGS. 5-8, an alternative viscosity measurement system 210 in accordance with various embodiments incorporates a magnetic torque sensing system instead of flexible cantilevered beams. As shown in FIGS. 5A-5B, mounted atop a cantilevered support member 220 is a pair of magnet support blocks 240a, 240b. Each magnet support block 240a, 240b has mounted thereon a fixed magnet 242a, 242b oriented in opposing polarity for repelling a strong magnet 275, such as a neodymium magnet, mounted to a first end 271 of a torque arm 270, the first end 271 extending between the pair of magnet support blocks 240a, 240b. The torque arm 270 is shown in detail in FIG. 6 and has a first end 271, a second end 272 and a central bore 273 that receives a rotatable torque transmitting shaft 260 therethrough. The torque arm 270 is fixedly mounted to the rotatable torque transmitting shaft 260 for rotation therewith.

Returning to FIGS. 5A-5B, in various embodiments, a torque transmitting shaft 260 rotatably mounts through, and extends downward from, the cantilevered support member 220. The cantilevered support member 220 effectively suspends the torque transmitting shaft 260 over a weighted base 225 to which the vertical support column 230 mounts. The weighted base 225 may, in various embodiments, provide stability to prevent vibration in the viscosity measurement system 210 during testing and thereby insures more accurate output. In various embodiments, the viscosity measurement system 210 weighs between ten (10) and sixty (60) pounds, preferably between twenty (20) and forty (40) pounds. In some embodiments the system weighs thirty-five (35) pounds, with the greatest portion of weight being distributed throughout the base 225 for added stability.

The weighted base 225 provides stability to prevent vibration in the system 210 during testing and thereby insures more accurate output. In various embodiments, a digital display member (not shown) is mounted to a free end of the cantilevered support member 220 or connected to the viscosity measurement system 210 via a computer network. Because the readout produced by the digital display member consists of digital indicia, the difficulties associated with reading measurement lines on a manually-read torsion spring activated scale are avoided. Accordingly, user error in reading a calculated viscosity measurement due to vibration can be eliminated by a viscosity measurement system 210 in accordance with various embodiments. It will be recognized by one of skill in the art that the various magnetic torque sensing aspects of the viscosity measurement system 210 can be incorporated into non-portable embodiments.

Rotation of the torque arm 270 by the torque transmitting shaft 260 pushes the strong magnet 275 toward one fixed magnet 242a or the other fixed magnet 242b such that a certain amount of magnetic resistance results between the strong magnet 275 and the fixed magnets 242a, 242b on the pair of magnet support blocks 240a, 240b. In other words, the magnetic field between the strong magnet 275 and the fixed magnets 242a, 242b resists the rotation of the torque arm 270 because the fixed magnets 242a, 242b are oriented such that their polarity is the same as that of both faces of the strong magnet 275 such that the magnets repel. The amount of torque applied to the rotatable torque shaft 260 during sample testing results from shear forces applied to a submerged bob (not shown) rotatably coupled to a spinning rotor (not shown) that captures a portion of fluid test sample therebetween. The magnetic torque arm 270 then deflects a certain pre-defined rotational amount per unit of torque transmitted by the rotatable torque shaft 260.

Figure 5A:
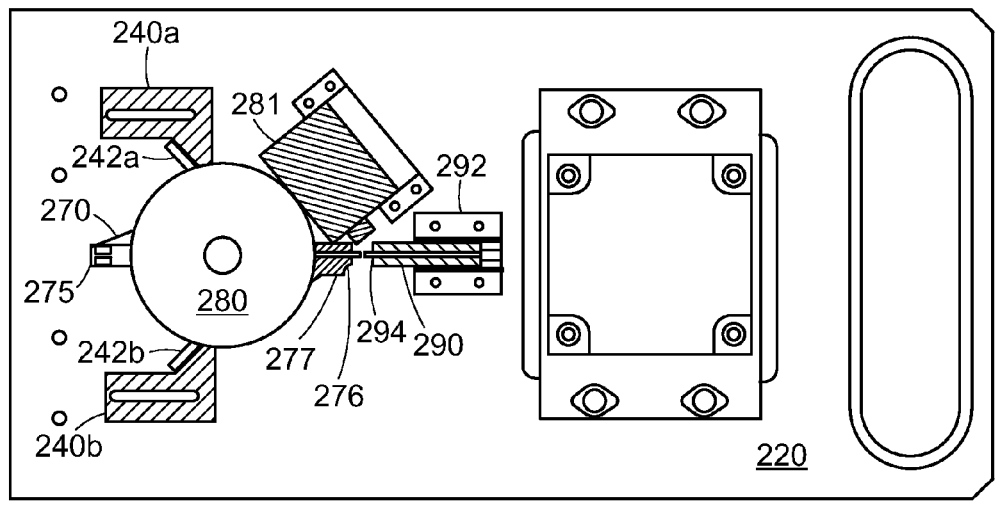
FIGS. 5A-5B are schematics illustrating top and side views of an alternative viscosity measurement system in accordance with various embodiments.
Figure 5B:
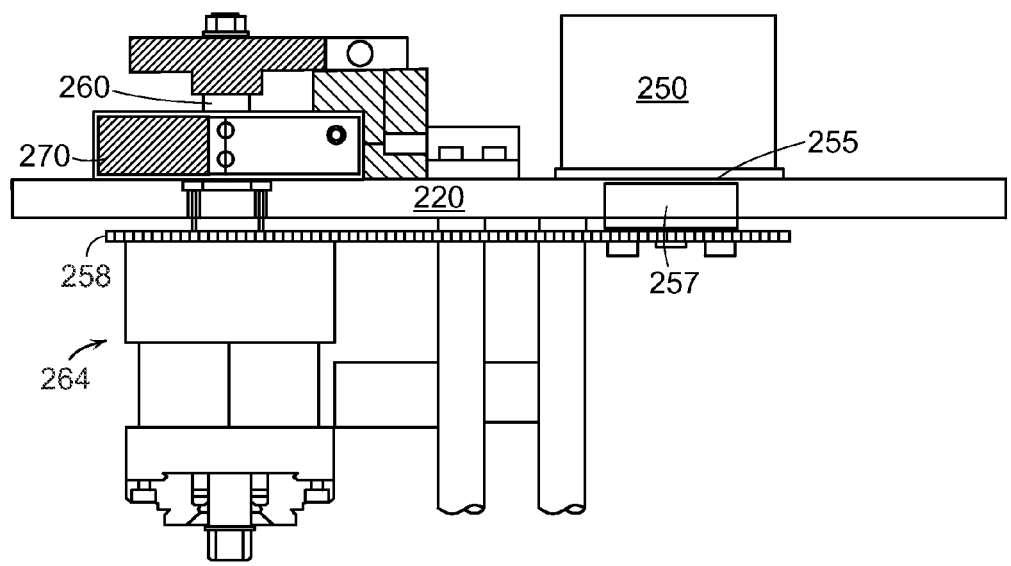
Figure 6:
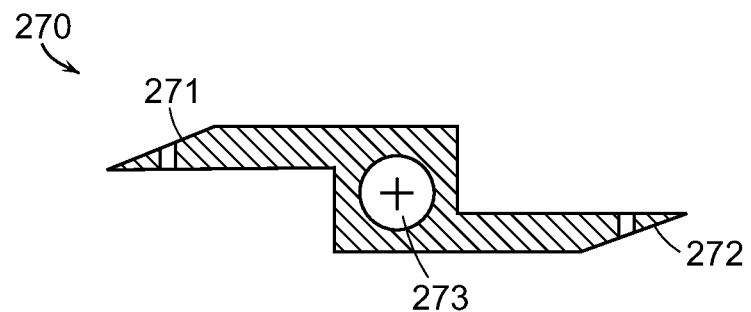
FIG. 6 is a schematic illustrating a portion of the alternative viscosity measurement system in accordance with various embodiments.

Although the magnet support blocks 240a, 240b and fixed magnets 242a, 242b are depicted in FIG. 5A as being disposed on the support surface 220 such that the fixed magnets 242a, 242b are aligned at approximately 45 degrees to the longitudinal axis of the torque arm 270, other spacing and orientations are contemplated by various embodiments of the present disclosure and represent design choice selections. Moving the magnetic support blocks 240a, 240b further away from the magnetic torque arm 270 results in requiring more deflection per unit of torque for making a measurement. Moving the magnet support blocks 240a, 240b further in toward the magnetic torque arm 270 results in requiring less deflection per unit of torque. If a test sample requires high torque measurements, the magnet support blocks 240a, 240b could be moved out to a wider spacing from the magnetic torque arm 270 and larger diameter fixed magnets 242a, 242b could be applied. Similarly, the magnet support blocks 240a, 240b could be moved inward for lighter torque readings and the diameter of the fixed magnets 242a, 242b could be reduced. In various embodiments, the magnet support blocks 240a, 240b are adjustable, thereby enabling a user to calibrate the system 210 to various setting for testing a range of viscosities.

Also mounted atop the cantilevered support member 220 is a variable speed drive 250 that is adapted for computer automated multistep sequencing through a range of rotational drive speeds (RPMs). The variable speed drive 250 has engaged therewith a drive shaft 255 extending downward through the cantilevered support member 220. The drive shaft 255 engages with a rotatable drive member 257 mounted beneath the cantilevered support member 220. The drive shaft 255 lies along an axis distinct from the axis of the torque transmitting shaft 260, and in various embodiments, the two axes are parallel to one another. In various embodiments, the two shafts are connected by a non-magnetic chain drive 258.

In various embodiments, the system further comprises a digital encoder 280 (e.g., optical or magnetic encoder) mounted atop the cantilevered support member 220 and coupled to the torque transmitting shaft 260 for producing an output signal that varies as a function of the degree of rotation of the torque transmitting shaft 260 and magnetic torque resistance force of the magnetic torque arm 270. Digital encoder 280 may be but is not limited to, similar to digital encoder 80 described above. An encoder sensor head 281 is located proximate to the digital encoder 280 for taking readings. Mounting the encoder 280 to the torque transmitting shaft 260 further adds space economy to the compact digital viscosity measurement system 210, which aids in portability and eliminates any additional moving parts, such as an encoder shaft and connection belt. Such additional elements would claim additional space, add weight, and present additional integrated moving parts that could seize or otherwise fail catastrophically in use under harsh testing environment conditions.

The accuracy of readings taken by the digital encoder 280 depends, in part, on the ability of the system 210 to zero the magnetic torque arm 270 precisely. Accordingly, the various embodiments depicted in FIGS. 5-8 optionally include a magnetized pin or shim 277 fixedly disposed in the second end 272 of the magnetic torque arm 270 to promote consistent zeroing. A balance pole 276 may be applied to the second end 272 of the magnetic torque arm 270 such that the first end 271 and second end 272 physically bear identically, or substantially similarly weighted items. This design contributes to accurately zeroing the magnetic torque arm 270. The rotating pin or shim 277 is magnetized by a magnet disposed behind the rotating pin or shim 277 (i.e., between the rotating pin or shim 277 and the rotatable torque transmitting shaft 260). In various embodiments, the rotating pin or shim 277 is a pin having a very sharp point to minimize the amount of travel necessary to move away from alignment with a target. In various embodiments the rotating pin or shim 277 is a pin made from a 400 series steel wire, or other magnetic material, that is machined to a sharp point. One non limiting example is 0.027 inch music wire ground to a sharp point.

Disposed on the support surface 220 adjacent to and directly facing the rotating pin or shim 277 is a fixed shim 294 fixedly mounted to a point holder 290 such that a gap between the rotating pin or shim 277 and the fixed shim 294 is no greater than 20 thousandths of an inch. The fixed shim 294 may be mounted, in various embodiments, on an adjustable holding mechanism for moving the fixed shim 294 back and forth to accommodate varying gaps between the rotating pin or shim 277 and fixed shim 294. The fixed shim 294 is in contact with, or in proximity of a magnet of opposite polarity than that applying a magnetic charge to the rotating pin or shim 277 such that the fixed shim 294 bears a magnetic charge that attracts the rotating pin or shim 277 into point-on-edge alignment. Like the rotating pin or shim 277, the fixed shim 294 is manufactured from a material capable of carrying a magnetic charge, such as 400 series stainless steel. Using a fixed shim 294 instead of a fixed pin provides a greater area over which the rotating pin or shim 277 may align itself back to zero. The use of a fixed pin instead of a fixed shim 294 is, of course, encompassed by various embodiments. For example, in various embodiments, the shim may be three thousandths of an inch thick. In another embodiment, the fixed shim 294 and rotating pin or shim 277 may be both pins of precisely machined tips for aligning the magnetic torque arm 270 along a precisely zero measurement position as determined by the rotating encoder 280. Although described with reference to FIGS. 5-8, it will be apparent in view of this disclosure that any magnetic torque sensing system may benefit from the addition of a magnetized shim or pin as described above, including for example, the embodiments described below with reference to FIGS. 9-10.

Figure 7:
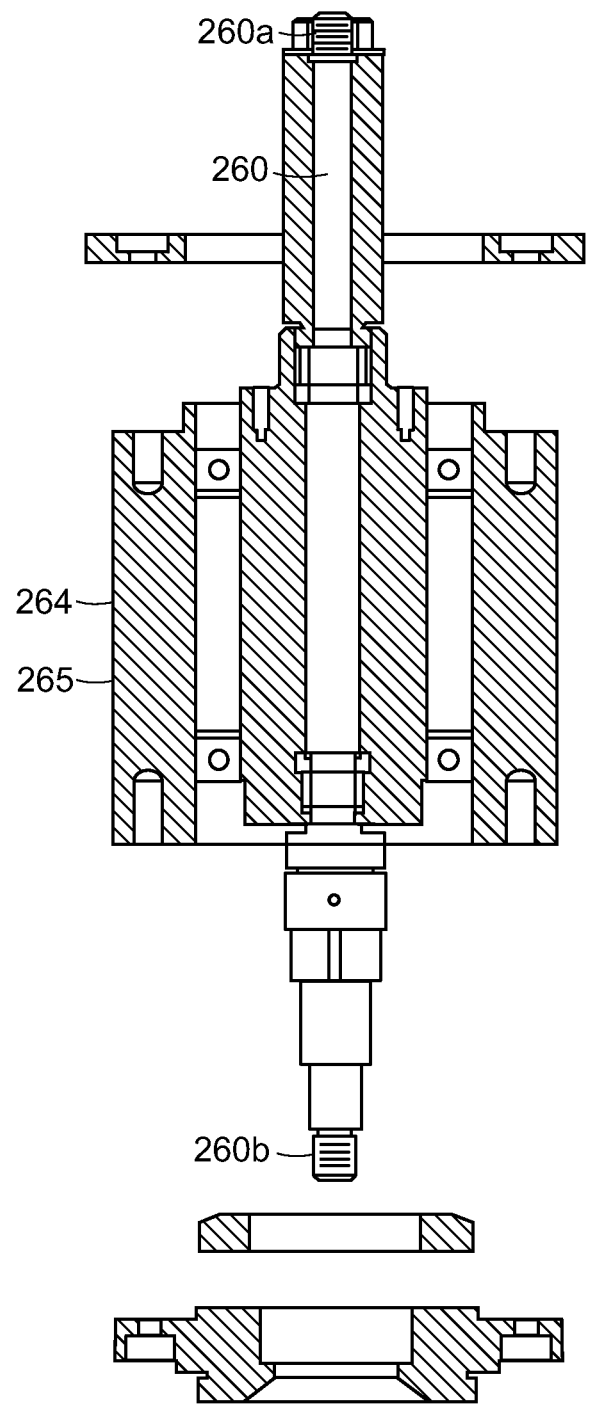
FIG. 7 is a schematic illustrating a top view of a portion of the alternative viscosity measurement system in accordance with various embodiments.

In operation, the digital viscosity measurement system 210 comprises elements that contact a test sample. A mechanical measurement device (not shown) applies torque to the torque transmitting shaft 260 when submerged in a fluid or viscous composition. In various embodiments, the measurement device comprises an API standard-compatible submersible bob member coupled to the lower end 260b (shown in FIG. 7) of the torque transmitting shaft 260 by a mechanical means, such as threads, and a submersible rotating sleeve member mounted about the torque-transmitting shaft 260 and bob member and coupled to the rotatable drive member 257. The rotating sleeve member may be indirectly or directly coupled via a drive coupling member 258 to the rotatable drive member 257. The drive coupling member 258 may be, for example, a belt or chain, such as a non-magnetic chain drive, engaged with the rotatable drive member 257 and coupled to the shaft assembly 265 (shown in FIG. 7). When the variable speed drive 250 and drive shaft 255 rotate, the rotatable drive member 257 thereon can then rotate the rotatable sleeve 262 via the drive coupling member 258 transmitting the rotational force. In some embodiments, the rotatable sleeve 262 may be directly coupled to a rotor shaft 264 (e.g., a barrel shaft concentric with and external to the torque transmitting shaft 260 as shown in FIG. 7), which is coupled to a rotatable drive member 257 via a drive coupling member 258. In such embodiments, the rotatable drive member 257 may rotate the rotor shaft 264 via drive coupling member 258, thereby rotating the rotatable sleeve 262.

Turning now to the particulars of the variable speed drive 250, the digital viscosity measurement system 210 in accordance with various embodiments provides substantial improvements over prior art viscosity testing devices. In various embodiments, the variable speed drive 250 may be for example, similar to the variable speed drive 50 described hereinabove. The integration of a computer controlled variable speed drive 250 mounted on a unique axis enables a user to program the digital viscosity measurement system 210 and run automatically through a series of speeds and time intervals to execute a series of required, industry standard and/or uniquely programmed tests. The programmability and computer control of the variable speed drive 250 enables accurate, efficiently measured test results. Additionally, the entirely digital composition of the viscosity measurement system 210 enables computer automation of multistep sequencing and bi-directional, oscillation testing, which is useful, for example, for testing a gel setting rate.

This precise, repeatable, and accurate controllability of the variable speed drive 250 stems in part from the variable speed drive 250 requiring no gearing changes and avoiding load issues associated with geared motors. The electronically controlled drive in the variable speed drive motor 250 produces a consist output with smooth transitions between drive shaft 255 rotational speeds. The highly controllable variable speed drive 250 may, in various embodiments, be functional through a large range of speeds while precisely achieving those desired speeds.

Figure 8A:
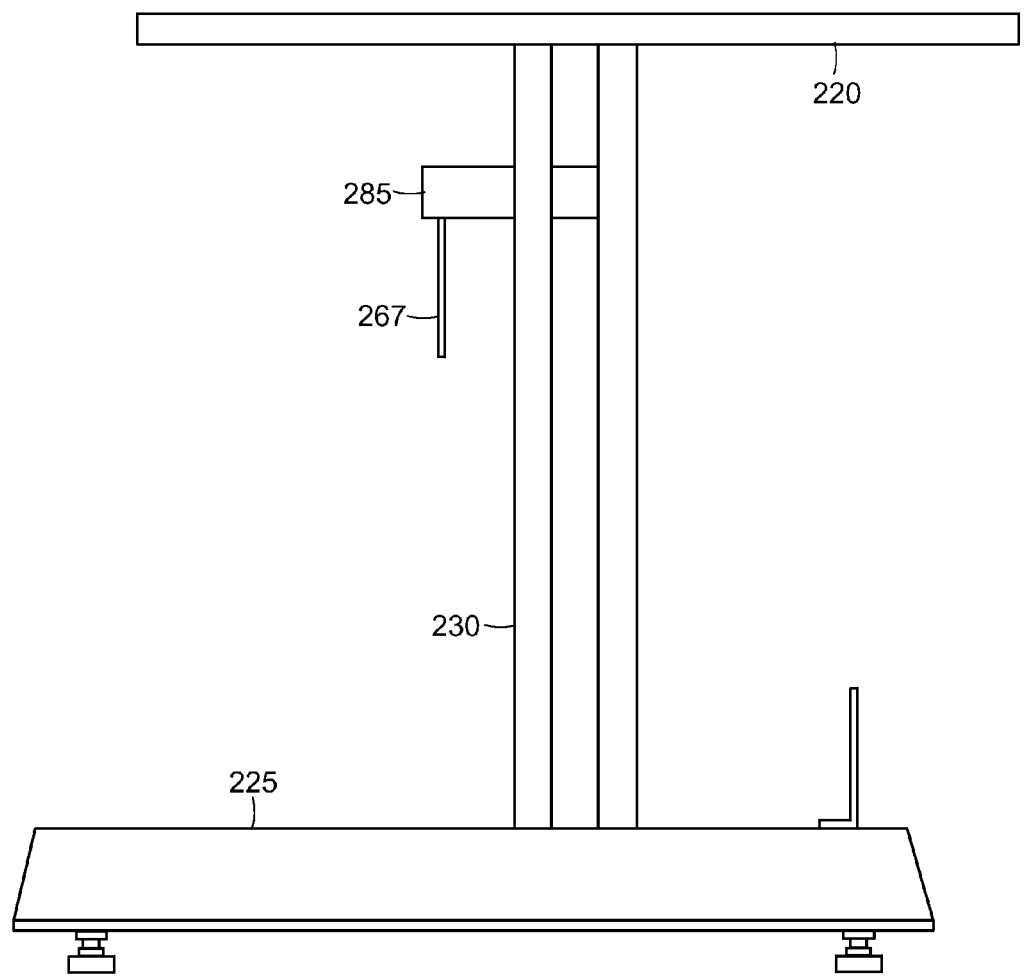
FIG. 8A is a schematic illustrating a side view of portion of the alternative viscosity measurement system in accordance with various embodiments.
Figure 8B:
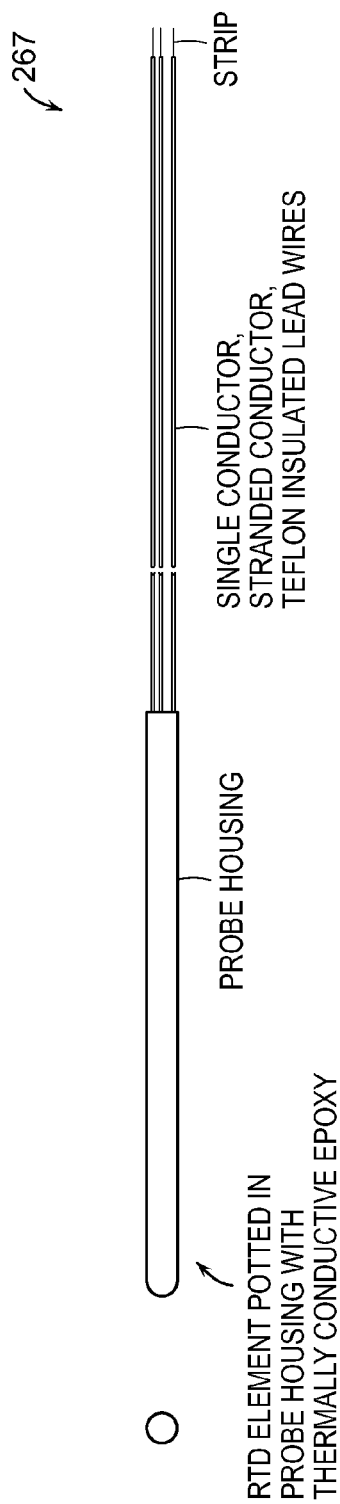
FIG. 8B is a schematic illustrating a resistance temperature detector style temperature probe system in accordance with various embodiments.
Figure 8B:
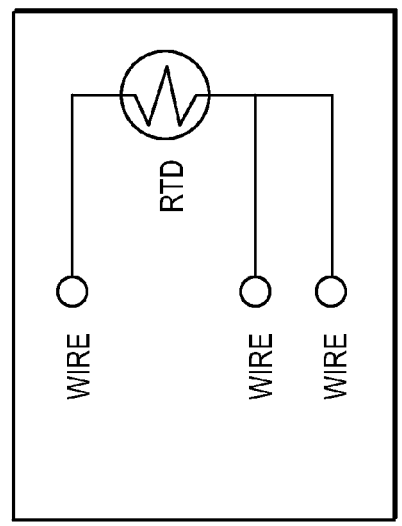

The system 210 may accommodate any number of sensors disposed thereon. For example, as indicated in various embodiments illustrated by FIGS. 8A-8B, a temperature probe bracket 285 may be mounted to the support column 230 for supporting a temperature probe 267 (e.g., a resistance temperature detector (RTD) as shown in FIG. 8B) submerged in the testing sample retained in a cup in which the rotor (e.g., 62 as shown in FIG. 1) and bob (e.g., 65 as shown in FIG. 1) assembly is submerged. In various alternate embodiments, a temperature sensor 267 may be disposed in the bob along with a wireless transmitter for wirelessly transmitting a temperature reading while submerged in a test sample. In such embodiments, the top portion of the bob housing the temperature sensor 267 and wireless transmitter may be manufactured of a non-metallic material to better allow transmission of the signal. This placement of a temperature probe 267 within the bob would enable a highly accurate measurement of the portion of the test sample located between the rotor and bob.

In addition to sensors, various embodiments contemplate using bearings that require little or no lubrication so as to reduce friction force. The bob and shaft assembly bearings may use, for example, LO 1 lubrication oil or the assembly may incorporate ceramic bearings that require no lubrication. Reducing friction may be advantageous, for example, because digital viscosity measurement systems 210 in accordance with various embodiments may exhibit a "dead zone", at least partially caused by friction in the viscosity measurement system 210, where no torque is registered by the encoder below a particular threshold (e.g., ±150 pulses for the digital incremental magnetic encoder described above with reference to FIGS. 2A-2D). Additional friction increases the size of this dead zone. Therefore, reducing friction forces contributes to the accuracy and sensitivity of the resistance reading taken when the torque shaft 260 rotates.

Figure 9A:
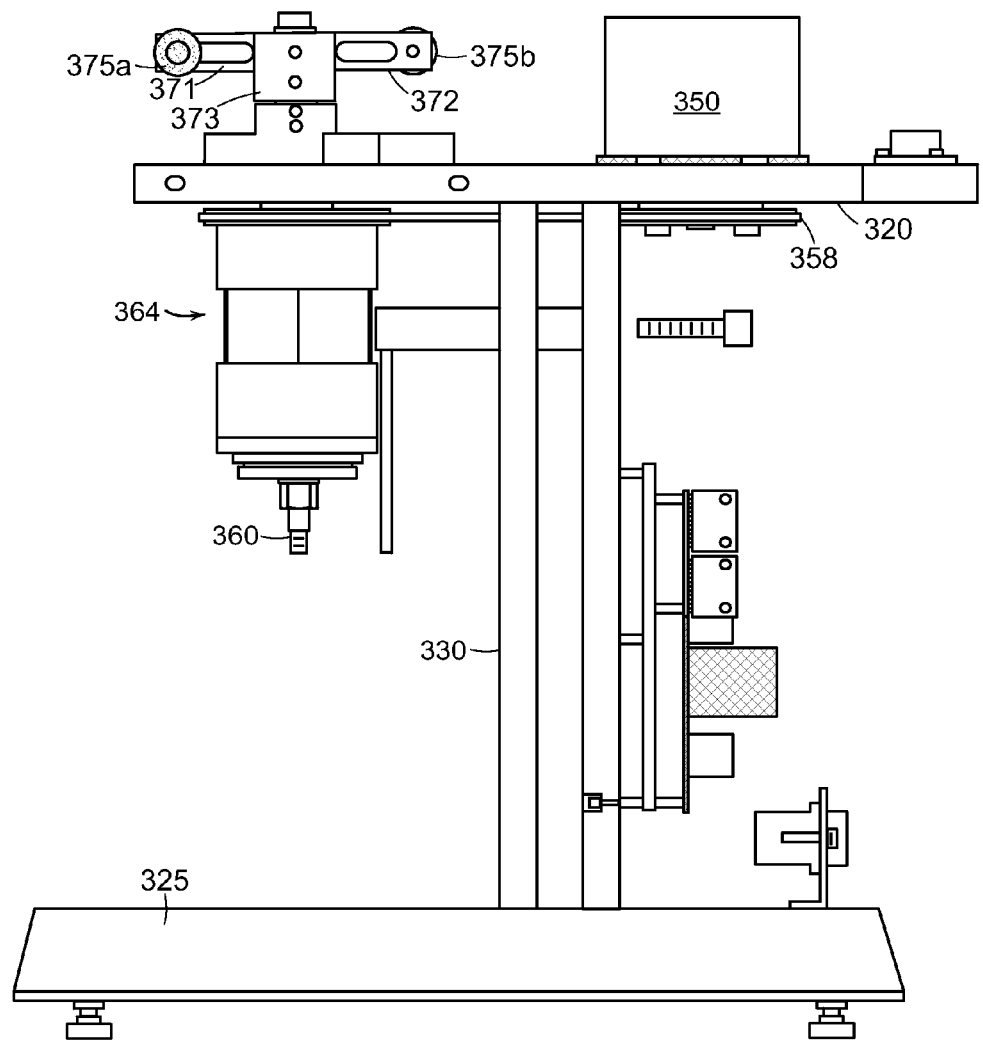
FIGS. 9A-9B are schematics illustrating side and top views of a second alternative viscosity measurement system in accordance with various embodiments.
Figure 9B:
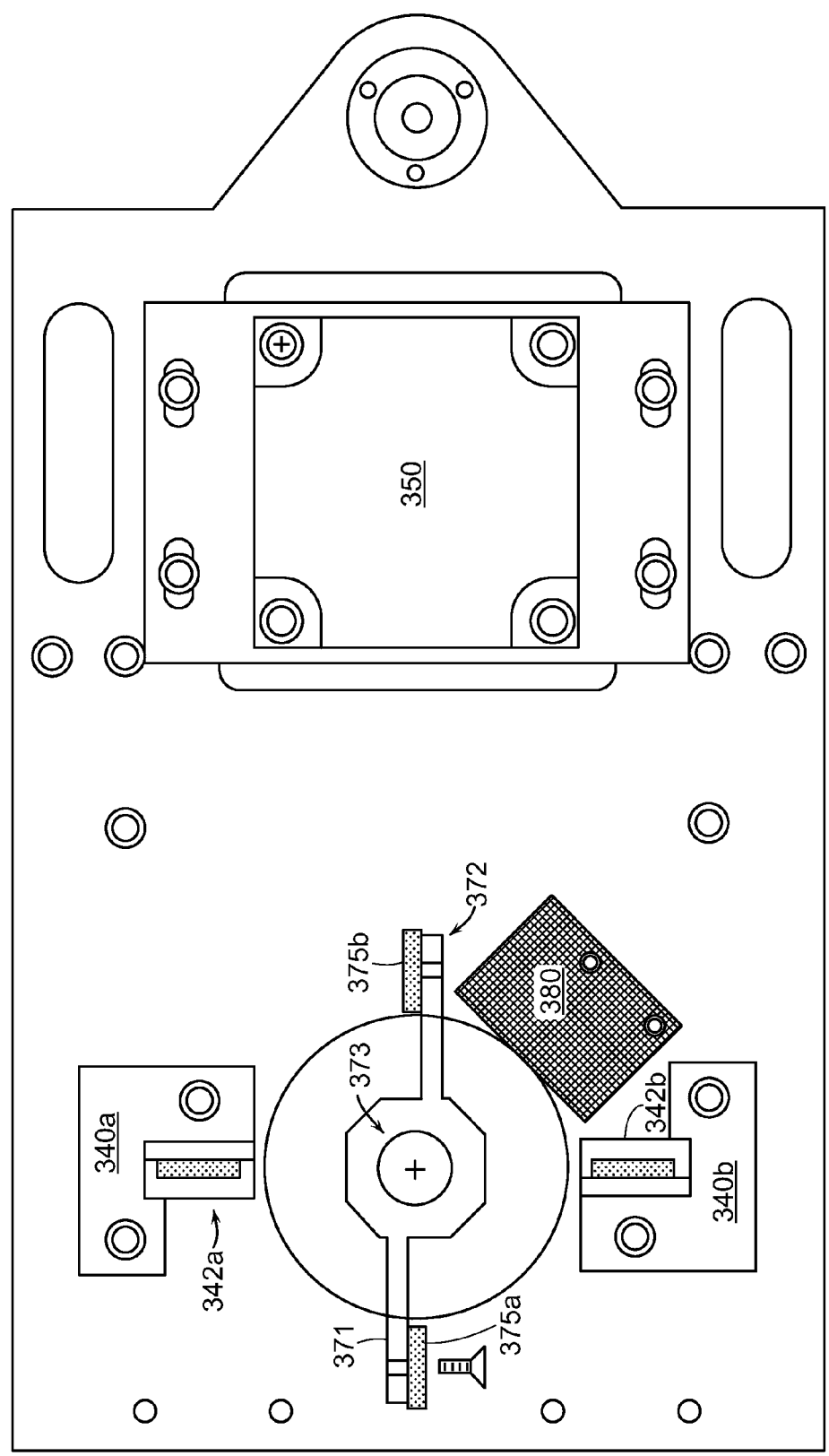
Figure 10A:
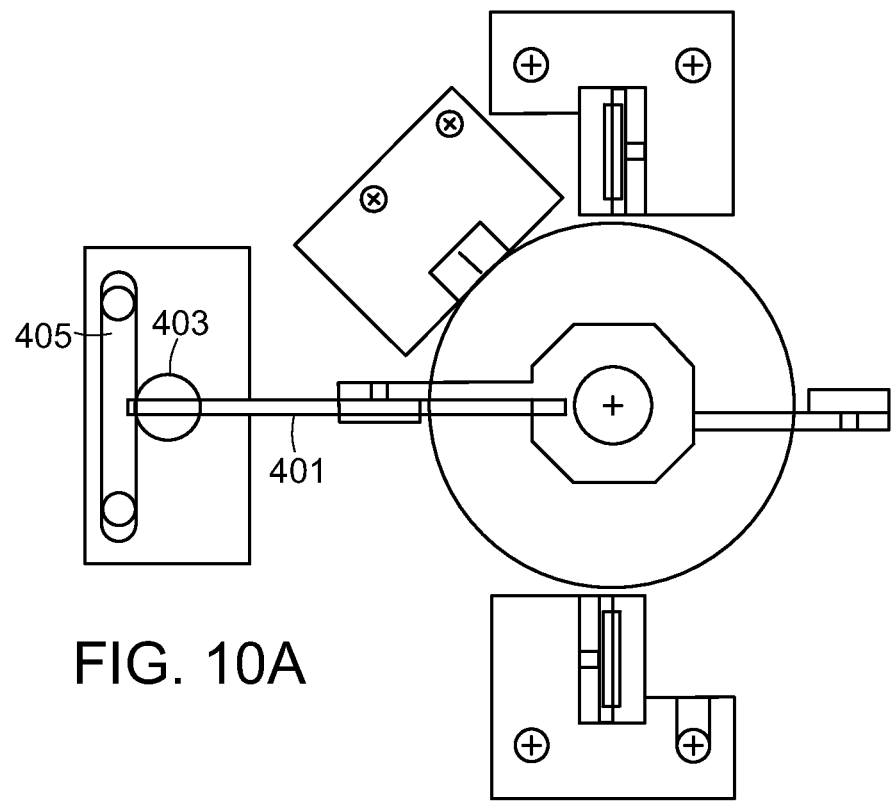
FIGS. 10A and 10B are schematics illustrating top and side views of a portion of the second alternative viscosity measurement system in accordance with various embodiments.
Figure 10B:
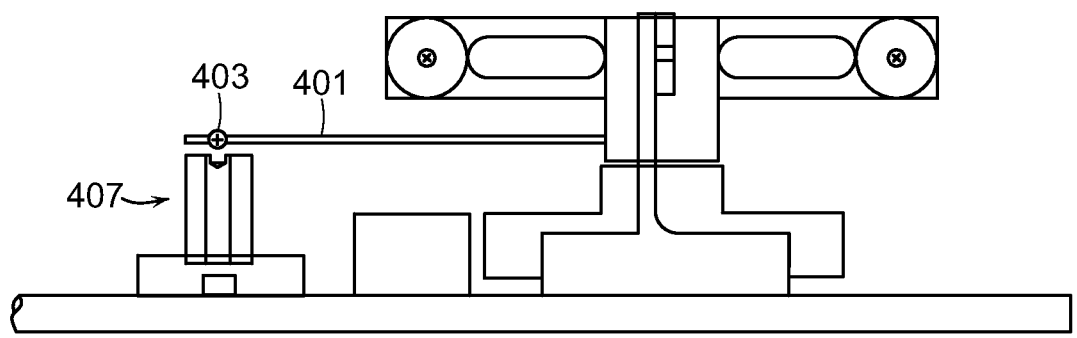

Turning now to FIGS. 9-10, another alternative viscosity measurement system 310 in accordance with various embodiments incorporates an alternative magnetic torque sensing system. As shown in FIGS. 9A-9B, mounted atop a cantilevered support member 320 is a pair of magnet support blocks 340a, 340b. Each magnet support block 340a, 340b has mounted thereon a fixed magnet 342a, 342b oriented in opposing polarity for repelling strong magnets 375a, 375b, such as neodymium magnets, mounted to each of a first end 371 and a second end 372 of a torque arm 370, each of the first end 371 and the second end 372 extending oppositely between the pair of magnet support blocks 340a, 340b. The torque arm has a first end 371, a second end 372 and a central bore 373 that receives a rotatable torque transmitting shaft 360 therethrough. The torque arm 370 is fixedly mounted to the rotatable torque transmitting shaft 360 for rotation therewith.

In various embodiments, a torque transmitting shaft 360 rotatably mounts through, and extends downward from, the cantilevered support member 320. The cantilevered support member 320 effectively suspends the torque transmitting shaft 360 over a weighted base 325 to which the vertical support column 330 mounts. The weighted base 325 may, in various embodiments, provide stability to prevent vibration in the viscosity measurement system 310 during testing and thereby insures more accurate output. In various embodiments, the viscosity measurement system 310 weighs between ten (10) and sixty (60) pounds, preferably between twenty (20) and forty (40) pounds. In some embodiments the system weighs thirty-five (35) pounds, with the greatest portion of weight being distributed throughout the base 325 for added stability.

The weighted base 325 provides stability to prevent vibration in the system 310 during testing and thereby insures more accurate output. In various embodiments, a digital display member (not shown) is mounted to a free end of the cantilevered support member 320 or connected to the viscosity measurement system 310 via a computer network. Because the readout produced by the digital display member consists of digital indicia, the difficulties associated with reading measurement lines on a manually-read torsion spring activated scale are avoided. Accordingly, user error in reading a calculated viscosity measurement due to vibration can be eliminated by a viscosity measurement system 310 in accordance with various embodiments. It will be recognized by one of skill in the art that the various magnetic torque sensing aspects of the viscosity measurement system 310 can be incorporated into non-portable embodiments.

Rotation of the torque arm 370 by the torque transmitting shaft 360 pushes the strong magnets 375a, 375b toward one fixed magnet 342a or the other fixed magnet 342b such that a certain amount of magnetic resistance results between the strong magnets 375a, 375b and the fixed magnets 342a, 342b on the pair of magnet support blocks 340a, 340b. In other words, the magnetic field between the strong magnets 375a, 375b and the fixed magnets 342a, 342b resists the rotation of the torque arm 370 because the fixed magnets 342a, 342b are oriented such that their polarity is the same as that of both faces of the strong magnets 375a, 375b such that the magnets repel. The amount of torque applied to the rotatable torque shaft 360 during sample testing results from shear forces applied to a submerged bob (not shown) rotatably coupled to a spinning rotor (not shown) that captures a portion of fluid test sample therebetween. The magnetic torque arm 370 then deflects a certain pre-defined rotational amount per unit of torque transmitted by the rotatable torque shaft 360.

Although the magnet support blocks 340a, 340b and fixed magnets 342a, 342b are depicted in FIGS. 9-10 as being disposed on the support surface 320 such that the fixed magnets 342a, 342b are aligned at approximately 90 degrees to the longitudinal axis of the torque arm 370, other spacing and orientations are contemplated by various embodiments of the present disclosure and represent design choice selections. Moving the magnetic support blocks 340a, 340b further away from the magnetic torque arm 370 results in requiring more deflection per unit of torque for making a measurement. Moving the magnet support blocks 340a, 340b further in toward the magnetic torque arm 370 results in requiring less deflection per unit of torque. If a test sample requires high torque measurements, the magnet support blocks 340a, 340b could be moved out to a wider spacing from the magnetic torque arm 370 and larger diameter fixed magnets 342a, 342b could be applied. Similarly, the magnet support blocks 340a, 340b could be moved inward for lighter torque readings and the diameter of the fixed magnets 342a, 342b could be reduced. In various embodiments, the magnet support blocks 340a, 340b are adjustable, thereby enabling a user to calibrate the system 310 to various setting for testing a range of viscosities.

Also mounted atop the cantilevered support member 320 is a variable speed drive 350 that is adapted for computer automated multistep sequencing through a range of rotational drive speeds (RPMs). The variable speed drive 350 has engaged therewith a drive shaft 355 extending downward through the cantilevered support member 320. The drive shaft 355 engages with a rotatable drive member 357 mounted beneath the cantilevered support member 320. The drive shaft 355 lies along an axis distinct from the axis of the torque transmitting shaft 360, and in various embodiments, the two axes are parallel to one another. In various embodiments, the two shafts are connected by a non-magnetic chain drive 358.

In various embodiments, the system further comprises a digital encoder 380 (e.g., optical or magnetic encoder) mounted atop the cantilevered support member 320 and coupled to the torque transmitting shaft 360 for producing an output signal that varies as a function of the degree of rotation of the torque transmitting shaft 360 and magnetic torque resistance force of the magnetic torque arm 370. Digital encoder 380 may be but is not limited to, similar to digital encoder 280 and/or digital encoder 80 as described hereinabove. An encoder sensor head 381 is located proximate to the digital encoder 380 for taking readings. Mounting the encoder 380 to the torque transmitting shaft 360 further adds space economy to the compact digital viscosity measurement system 310, which aids in portability and eliminates any additional moving parts, such as an encoder shaft and connection belt. Such additional elements would claim additional space, add weight, and present additional integrated moving parts that could seize or otherwise fail catastrophically in use under harsh testing environment conditions.

The accuracy of readings taken by the digital encoder 380 depends, in part, on the ability of the system 310 to zero the magnetic torque arm 370 precisely. Accordingly, the various embodiments depicted in FIG. 10A-10B optionally include an electromagnetic positioning assembly 400 to promote consistent zeroing. A magnetic spring arm 401 may be affixed to the central bore 373 of the magnetic torque arm 370 such that the magnetic spring arm 401 is substantially parallel to the second end 372 of the magnetic torque arm 370. In various embodiments, a magnetic positioning element 403 (e.g., a ball as shown) may be affixed to the magnetic spring arm in vertical alignment with an adjustable receiving slot 405 defined on the upper surface of an electromagnet 407. The magnetic positioning element 403 is preferably manufactured from a material capable of carrying a magnetic charge, such as 400 series stainless steel. The electromagnet 407 is preferably a magnet of opposite polarity than that of the magnetic positioning element 403 such that the electromagnet 407 bears a magnetic charge that attracts the magnetic positioning element 403 into engagement with the adjustable receiving slot 405. This design contributes to accurately zeroing the magnetic torque arm 370. In various embodiments, the electromagnet 407 may be magnetized by a current, thereby drawing the positioning element 403 into the adjustable receiving slot 405. In various embodiments, drawing the positioning element into the adjustable receiving slot 405 causes magnetic spring arm 401 to rotate magnetic torque arm 370 into a zeroed position. Although described with reference to FIG. 10A-10B, it will be apparent in view of this disclosure that any magnetic torque sensing system may benefit from the addition of a magnetized shim or pin as described above, including for example, the embodiments described above with reference to FIGS. 5-9.

For various embodiments requiring only unidirectional torque measurements, a physical stop (not shown) may optionally be placed in a rotational path of the magnetic torque arm 370 to provide a consistent zeroing position of the torque transmitting shaft 360. Such a configuration may be advantageous for particularly sensitive torque measuring applications (e.g., those requiring accuracy to $\frac{1}{1,000}$ oz.-in or $\frac{1}{10,000}$ oz-in. In such applications a physical stop may advantageously be positioned to create a slight bias (e.g., at least 150 pulses from a true zero point) to overcome the dead zone described hereinabove. It will be apparent in view of this disclosure that such a physical stop may be used by any of the various embodiments described herein with reference to FIGS. 1-10.

Referring again to FIGS. 9A-9B, in operation, the digital viscosity measurement system 310 comprises elements that contact a test sample. A mechanical measurement device (not shown) applies torque to the torque transmitting shaft 360 when submerged in a fluid or viscous composition. In various embodiments, the measurement device comprises an API standard-compatible submersible bob member coupled to the lower end of the torque transmitting shaft 360 by a mechanical means, such as threads, and a submersible rotating sleeve member mounted about the torque-transmitting shaft 360 and bob member and coupled to the rotatable drive member 357. The rotating sleeve member may be indirectly or directly coupled via a drive coupling member 258 to the rotatable drive member 357. The drive coupling member 358 may be, for example, a belt or chain, such as a non-magnetic chain drive, engaged with the rotatable drive member 357 and coupled to the shaft assembly 365. When the variable speed drive 350 and drive shaft 355 rotate, the rotatable drive member 357 thereon can then rotate the rotatable sleeve 362 via the drive coupling member 358 transmitting the rotational force. In some embodiments, the rotatable sleeve 262 may be directly coupled to a rotor shaft 364 (e.g., a barrel shaft concentric with and external to the torque transmitting shaft 360 as shown in FIG. 7), which is coupled to a rotatable drive member 357 via a drive coupling member 358. In such embodiments, the rotatable drive member 357 may rotate the rotor shaft 364 via drive coupling member 358, thereby rotating the rotatable sleeve 362.

Turning now to the particulars of the variable speed drive 350, the digital viscosity measurement system 310 in accordance with various embodiments provides substantial improvements over prior art viscosity testing devices. In various embodiments, the variable speed drive 350 may be for example, similar to the variable speed drive 50 and/or the variable speed drive 250 described hereinabove. The integration of a computer controlled variable speed drive 350 mounted on a unique axis enables a user to program the digital viscosity measurement system 310 and run automatically through a series of speeds and time intervals to execute a series of required, industry standard and/or uniquely programmed tests. The programmability and computer control of the variable speed drive 350 enables accurate, efficiently measured test results. Additionally, the entirely digital composition of the viscosity measurement system 310 enables computer automation of multistep sequencing and bi-directional, oscillation testing, which is useful, for example, for testing a gel setting rate.

This precise, repeatable, and accurate controllability of the variable speed drive 350 stems in part from the variable speed drive 350 requiring no gearing changes and avoiding load issues associated with geared motors. The electronically controlled drive in the variable speed drive motor 350 produces a consist output with smooth transitions between drive shaft 355 rotational speeds. The highly controllable variable speed drive 350 may, in various embodiments, be functional through a large range of speeds while precisely achieving those desired speeds.

The system 310 may accommodate any number of sensors disposed thereon. For example, as indicated in various embodiments illustrated by FIGS. 9A-9B, a temperature probe bracket 385 may be mounted to the support column 330 for supporting a temperature probe 367 (e.g., a resistance temperature detector (RTD) as shown in FIG. 8B) submerged in the testing sample retained in a cup in which the rotor (e.g., 62 as shown in FIG. 1) and bob (e.g., 65 as shown in FIG. 1) assembly is submerged. In various alternate embodiments, a temperature sensor 367 may be disposed in the bob along with a wireless transmitter for wirelessly transmitting a temperature reading while submerged in a test sample. In such embodiments, the top portion of the bob housing the temperature sensor 367 and wireless transmitter may be manufactured of a non-metallic material to better allow transmission of the signal. This placement of a temperature probe 367 within the bob would enable a highly accurate measurement of the portion of the test sample located between the rotor and bob.

In addition to sensors, various embodiments contemplate using bearings that require little or no lubrication so as to reduce friction force. The bob and shaft assembly bearings may use, for example, LO 1 lubrication oil or the assembly may incorporate ceramic bearings that require no lubrication. Reducing friction forces contributes to the accuracy and sensitivity of the resistance reading taken when the torque shaft 360 rotates.

Figure 11:
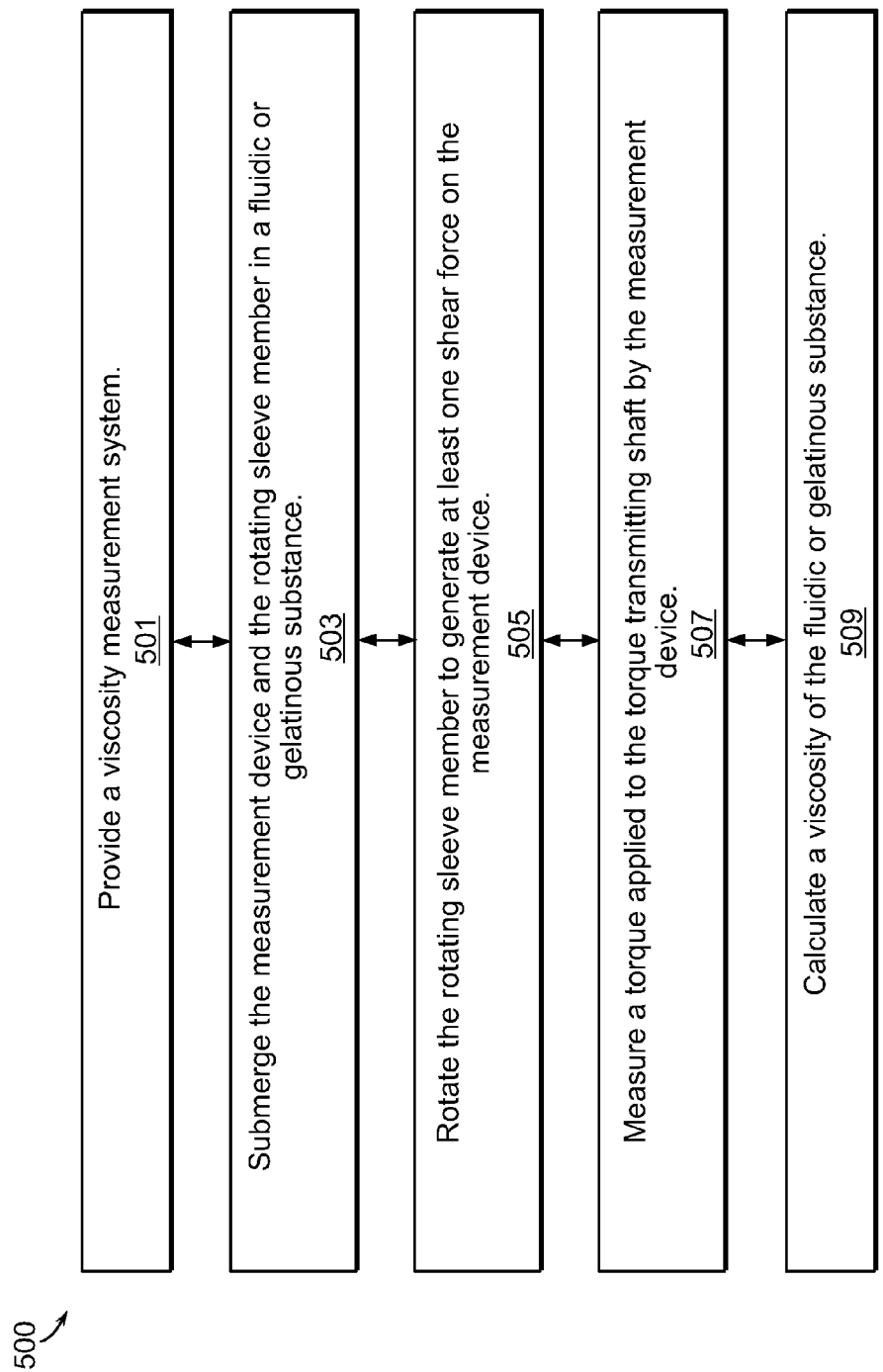
FIG. 11 is a flow chart illustrating methods for testing a viscosity of a fluidic or gelatinous substance in accordance with various embodiments.

Referring now to FIG. 11, a method for testing a viscosity of a fluidic or gelatinous substance 500 is illustrated. The method includes providing a viscosity measurement system 501, submerging the measurement device and the rotating sleeve member in a fluidic or gelatinous substance 503, rotating the rotating sleeve member to generate at least one shear force on the measurement device 505, measuring a torque applied to the torque transmitting shaft by the measurement device 507, and calculating a viscosity of the fluidic or gelatinous substance 509.

Providing a viscosity measurement system 501 may, in accordance with various embodiments may include providing any viscosity measurement system 10, 210, 310 described herein with reference to FIGS. 1-10. Submerging the measurement device and the rotating sleeve member in a fluidic or gelatinous substance 503 may be performed by filling a test cup or other vessel with the fluidic or gelatinous substance and positioning the test cup relative to the viscosity testing system. Rotating the rotating sleeve member to generate at least one shear force on the measurement device 505 may be performed by driving a variable speed motor 50, 250, 350 as described above with reference to FIGS. 1-10. Measuring a torque applied to the torque transmitting shaft by the measurement device 507 may be performed by use of a digital encoder 80, 280, 380 as described above with reference to FIGS. 1-10. Calculating a viscosity of the fluidic or gelatinous substance 509 may be performed by a processor (e.g., 85) in communication with the variable speed motor and the encoder as described above with reference to FIGS. 2-4.

The method may also include, in various embodiments, displaying a viscosity value on a digital display member such as digital display member 90 described above with reference to FIGS. 1-2. The method may also include transmitting a value of the viscosity to a remote receiver, which may be performed using a processor 85 and/or various computing equipment as described above with reference to FIGS. 2-4.

It is noted that the foregoing examples have been provided merely for the purpose of explanation and are in no way to be construed as limiting of the present disclosure. While the present invention has been described herein with reference to various exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A digital viscosity measurement system comprising:
a variable speed drive operatively coupled to a drive shaft;

a drive coupling member for operatively coupling a rotating sleeve member to the drive shaft;

a measurement device positioned concentric with the rotating sleeve member and coupled to a lower portion of a torque transmitting shaft, the torque transmitting shaft rotatably coupled with the measurement device;

a support surface oriented perpendicularly to the torque transmitting shaft;

a torque sensing device comprising: opposite polarity fixed magnets fixed to the support surface and positioned on opposite sides of a movable magnet;

a torque arm configured to be rotated by the torque transmitting shaft and disposed between the opposite polarity fixed magnets, the torque arm having a first end distal to the torque transmitting shaft with the movable magnet disposed thereon between the opposite polarity fixed magnets and a second end connected to the torque transmitting shaft, wherein rotation of the torque transmitting shaft moves the torque arm and moveable magnet toward one fixed magnet; and, a digital encoder configured to measure a torque applied to the torque transmitting shaft by the measurement device as ascertained by the force generated between the movable magnet and the one fixed magnet.

2. The digital viscosity measurement system of claim 1, further comprising a processor mounted to the digital viscosity measurement system in communication with the variable speed drive for varying speed and in communication with the encoder for calculating viscosity based on a measured magnitude of torque applied to the torque transmitting shaft by one or more shear forces arising between the rotating sleeve member and the measurement device.

3. The digital viscosity measurement system of claim 2, further comprising an electronic display member in communication with the processor for displaying a viscosity output and enabling selective control of the variable speed drive.

4. The digital viscosity measurement system of claim 1, wherein the measurement device comprises an American Petroleum Institute (API) standard-compatible submersible bob member.

5. The digital viscosity measurement system of claim 1, further comprising a temperature probe positioned adjacent to the rotating sleeve member.

6. The digital viscosity measurement system of claim 1, further comprising:

a rotatable magnetized member extending from a second end of the magnetic arm;

a fixed magnetized member disposed adjacent the rotatable magnetized member and having an opposite polarity than the rotatable magnetized member such that the rotatable magnetized member is attached to the fixed magnetized member for zeroing a rotation of the torque transmitting shaft.

7. The digital viscosity measurement system of claim 6, wherein the fixed magnetized member and the rotatable magnetized member are each selected from a group consisting of a magnetized shim and a magnetized needle.

8. The digital viscosity measurement system of claim 1, wherein the digital encoder produces an output signal that varies as a function of a degree of rotation of the torque transmitting shaft and of a known torque required to cause relative deflection movement of the torque arm.

9. The digital viscosity measurement system of claim 1, further comprising a second moveable magnet disposed on a second end of the torque arm between the opposite polarity magnets.

10. A method for testing a viscosity of a fluidic or gelatinous substance comprising:

providing a viscosity measurement system, the viscosity measurement system including:

a variable speed drive operatively coupled to a drive shaft;

a drive coupling member for operatively coupling a rotating sleeve member to the drive shaft;

a measurement device positioned concentric with the rotating sleeve member and coupled to a lower portion of a torque transmitting shaft, the torque transmitting shaft rotatably coupled with the measurement device, and;

a support surface oriented perpendicularly to the torque transmitting shaft;

a torque sensing device comprising: opposite polarity fixed magnets fixed to the support surface and positioned on opposite sides of a movable magnet;

a torque arm configured to be rotated by the torque transmitting shaft and disposed between the opposite polarity fixed magnets, the torque arm having a first end distal to the torque transmitting shaft with the moveable magnet disposed thereon between the opposite fixed polarity magnets and a second end connected to the torque transmitting shaft, wherein rotation of the torque transmitting shaft moves the torque arm and the movable magnet toward one fixed magnet; and, a digital encoder configured to measure a torque applied to the torque transmitting shaft by the measurement device as ascertained by the force generated between the movable magnet and the one fixed magnet;

submerging the measurement device and the rotating sleeve member in a fluidic or gelatinous substance;

rotating the rotating sleeve member to generate at least one shear force on the measurement device;

measuring, using the digital encoder, a torque applied to the torque transmitting shaft by the measurement device; and calculating, on a processor, a viscosity of the fluidic or gelatinous substance based on the rotational speed of the rotating sleeve member and the torque measured by the encoder.

11. The method of claim 10, further comprising displaying a value of the viscosity on a digital display member.

12. The method of claim 10, further comprising transmitting a value of the viscosity to a remote receiver.

13. The digital viscosity measurement system of claim 1, wherein said digital encoder is configured to measure a torque applied to the torque transmitting shaft by the measurement device.

* * * * *